(12) United States Patent
Ovenden

(10) Patent No.: US 11,908,559 B2
(45) Date of Patent: Feb. 20, 2024

(54) MEDICAL SUPPLY CABINET WITH MEDICAL SUPPLY CONTENTS HAVING RADIO FREQUENCY IDENTIFICATION TAGS

(71) Applicant: Aero Healthcare (US), LLC, Valley Cottage, NY (US)

(72) Inventor: Timothy John Ovenden, Upper Saddle River, NJ (US)

(73) Assignee: Aero Healthcare (US), LLC, Valley Cottage, NY (US)

( * ) Notice: Subject to any disclaimer, the term of this patent is extended or adjusted under 35 U.S.C. 154(b) by 183 days.

(21) Appl. No.: 17/468,802

(22) Filed: Sep. 8, 2021

(65) Prior Publication Data

US 2022/0068455 A1    Mar. 3, 2022

Related U.S. Application Data

(63) Continuation-in-part of application No. 17/062,044, filed on Oct. 2, 2020, now abandoned.

(60) Provisional application No. 62/912,162, filed on Oct. 8, 2019.

(51) Int. Cl.
*G16H 20/10* (2018.01)
*G06Q 10/0875* (2023.01)
*G06K 7/10* (2006.01)

(52) U.S. Cl.
CPC ......... *G16H 20/10* (2018.01); *G06K 7/10237* (2013.01); *G06Q 10/0875* (2013.01)

(58) Field of Classification Search
CPC .. G06Q 10/109; G06Q 10/0875; G16H 20/10; G06K 7/10237
See application file for complete search history.

(56) References Cited

U.S. PATENT DOCUMENTS

| | | |
|---|---|---|
| 794,405 A | 7/1905 | Henry |
| 796,600 A | 8/1905 | McLane et al. |
| 855,767 A | 6/1907 | Gibson |
| 947,967 A | 2/1910 | Gardner |
| 1,700,924 A | 2/1929 | Cushman |
| 2,093,530 A | 9/1937 | Walmsley |
| 2,530,220 A | 11/1950 | Belcher |
| 3,207,421 A | 9/1965 | Hunger et al. |
| 3,220,788 A | 11/1965 | Hunckler |
| 4,591,215 A | 5/1986 | Robbins |
| 4,949,843 A | 8/1990 | Stokes |
| D429,897 S | 8/2000 | Rogman et al. |

(Continued)

OTHER PUBLICATIONS

Nadeau, "Inclusion Collusion", Oct. 2017, https://www.hpnonline.com/sourcing-logistics/article/13000910/inclusion-collusion (Year: 2017).*

*Primary Examiner* — Allen C Chein
(74) *Attorney, Agent, or Firm* — Erise IP, P.A.

(57) ABSTRACT

A medical supply cabinet includes a housing; a medical supply cabinet identifying radio frequency identification tag located on the housing; and a plurality of medical supply packages, each medical supply package containing a specific medical supply. Each medical supply package includes a discarded portion created when the medical supply package is opened. The discarded portion of the medical supply package includes a medical supply package radio frequency identification tag identifying the specific medical supply associated with the medical supply package.

20 Claims, 19 Drawing Sheets

(56) References Cited

U.S. PATENT DOCUMENTS

| | | |
|---|---|---|
| 6,915,952 B1 | 7/2005 | Allen |
| 7,537,168 B2 | 5/2009 | Anderson et al. |
| 8,434,834 B2 | 5/2013 | Freimuth |
| 9,449,296 B2 | 9/2016 | MacDonald et al. |
| 2008/0185946 A1 | 8/2008 | Meckert et al. |
| 2009/0295260 A1 | 12/2009 | Brink |
| 2010/0106588 A1* | 4/2010 | Jones ............... G06Q 30/0223 709/248 |
| 2011/0037360 A1 | 2/2011 | Jakins et al. |
| 2013/0328661 A1* | 12/2013 | Phillips ............... G06F 3/0486 715/769 |
| 2014/0291397 A1* | 10/2014 | Caputo ............... G16H 15/00 235/385 |
| 2015/0366344 A1 | 12/2015 | Suggs |
| 2018/0317647 A1 | 11/2018 | Felsenthal et al. |
| 2019/0378602 A1* | 12/2019 | LaTorraca ............... A47F 10/02 |

\* cited by examiner

MEDICAL SUPPLY CABINET WITH MEDICAL SUPPLY CONTENTS HAVING RADIO FREQUENCY IDENTIFICATION TAGS

PRIORITY INFORMATION

The present application is a continuation-in-part of U.S. patent application Ser. No. 17/062,044, filed on Oct. 2, 2020, and claims priority, under 35 U.S.C. § 120, from U.S. patent application Ser. No. 17/062,044, filed on Oct. 2, 2020; said U.S. patent application Ser. No. 17/062,044, filed on Oct. 2, 2020, claims priority, under 35 U.S.C. § 119(e), from U.S. Provisional Patent Application, Ser. No. 62/912,162, filed on Oct. 8, 2019.

The present application claims priority, under 35 U.S.C. § 119(e), from U.S. Provisional Patent Application, Ser. No. 62/912,162, filed on Oct. 8, 2019.

The entire content of U.S. patent application Ser. No. 17/062,044, filed on Oct. 2, 2020, is hereby incorporated by reference. The entire content of U.S. Provisional Patent Application, Ser. No. 62/912,162, filed on Oct. 8, 2019, is hereby incorporated by reference.

BACKGROUND

A conventional medical supply cabinet 1, as illustrated in FIG. 1, includes a cabinet storage volume 3 and a door 2. The cabinet storage volume 3 includes various shelves 4, on which medical supplies can be placed and stored.

One issue with such a conventional medical supply cabinet is to know what supplies are needed for the medical supply cabinet to be properly stocked for the location that medical supply cabinet is servicing.

For example, if the medical supply cabinet needs a burn wound medical kit, an instant ice pack, an eye wound medical kit to be properly stock, in compliance with local or federal safety laws and regulations, the conventional medical supply cabinet 1 of FIG. 1 fails to have a system or mechanism to communicate what medical supplies have been exhausted and need to be replenished to bring the conventional medical supply cabinet 1 of FIG. 1 back into compliance with local or federal safety laws and regulations.

Moreover, the conventional medical supply cabinet 1 of FIG. 1 and conventional system of restocking fails to provide a mechanism to ensure that the conventional medical supply cabinet 1 of FIG. 1 has been replenished and is in compliance with local or federal safety laws and regulations.

Another issue with such a conventional medical supply cabinet is that shelves are not necessarily the best apparatus to store certain medical supplies.

For example, if the conventional medical supply cabinet 1 of FIG. 1 was required to have a supply antiseptic wipes, placing the antiseptic wipes on a shelf 4 may result in the antiseptic wipes being in an orientation so that a user cannot readily recognize the antiseptic wipes without removing the antiseptic wipes from the shelf 4.

On the other hand, placing the antiseptic wipes on a shelf 4 may result in the antiseptic wipes being accidently moved to a position behind a larger unit of medical supply so that a user cannot readily see the antiseptic wipes on the shelf 4 and mistakenly order more unnecessary antiseptic wipes.

Additionally, the conventional medical supply cabinet fails to effectively communicate to the party responsible for replenishing the conventional medical supply cabinet that a portion of a certain medical supply may have been used, thereby bringing the medical supply cabinet out of compliance with local or federal safety laws and regulations.

Lastly, the conventional medical supply cabinet fails to effectively communicate to the party responsible for replenishing the conventional medical supply cabinet which medical supplies have expired, thereby bringing the medical supply cabinet out of compliance with local or federal safety laws and regulations.

Therefore, it is desirable to provide a medical supply cabinet and restocking system that effectively communicates with machine readable codes what medical supplies have been exhausted and need to be replenished.

It is also desirable to provide a medical supply cabinet and restocking system that effectively communicates with machine readable codes what medical supplies have expired and need to be replenished.

It is further desirable to provide a medical supply cabinet and restocking system that effectively communicates with machine readable codes what medical supplies have caused the medical supply cabinet to be out of compliance with local or federal safety laws and regulations.

Also, it is desirable to provide a medical supply cabinet and restocking system that effectively communicates with machine readable code and human discernible symbols what medical supplies have been exhausted and need to be replenished.

Moreover, it is desirable to provide a medical supply cabinet and restocking system that effectively and error-free communicates with the party responsible for replenishing the medical supply cabinet what medical supplies have been exhausted and need to be replenished.

It is desirable to provide a medical supply cabinet and restocking system that effectively and error-free communicates with the party responsible for replenishing the medical supply cabinet what medical supplies have expired and need to be replenished.

It is also desirable to provide a medical supply cabinet and restocking system that effectively and error-free communicates with the party responsible for replenishing the medical supply cabinet what medical supplies have caused the medical supply cabinet to be out of compliance with local or federal safety laws and regulations.

It is desirable to provide a medical supply cabinet and restocking system that effectively communicates with RFID chips what medical supplies have been exhausted and need to be replenished.

It is also desirable to provide a medical supply cabinet and restocking system that effectively communicates with RFID chips what medical supplies have expired and need to be replenished.

It is further desirable to provide a medical supply cabinet and restocking system that effectively communicates with RFID chips what medical supplies have caused the medical supply cabinet to be out of compliance with local or federal safety laws and regulations.

Additionally, it is desirable to provide a medical supply cabinet that includes a mechanism to effectively store medical supplies that are not conducive to storage on a shelf.

Furthermore, it is desirable to provide a medical supply cabinet that includes a mechanism that attaches to the door to effectively store medical supplies that are not conducive to storage on a shelf.

Moreover, it is desirable to provide a medical supply cabinet that includes a mechanism that attaches to the door to effectively store medical supplies that are not conducive to storage on a shelf and that the mechanism includes machine readable code to effectively communicates what medical supplies have been exhausted and need to be replenished.

It is further desirable to provide a medical supply cabinet that includes a mechanism that attaches to the door to effectively store medical supplies that are not conducive to storage on a shelf and that the mechanism includes machine readable code and human discernible symbols to effectively communicates what medical supplies have been exhausted and need to be replenished.

It is also desirable to provide a medical supply cabinet and restocking system that utilizes packaging with tear-off portions that contain a RFID chip so that the absence of the tear-off portion containing the RFID chip indicates that the associated medical supply needs replenishing or is out of compliance with local or federal safety laws and regulations.

It is further desirable to a medical supply cabinet and restocking system that utilizes packaging with shrink warp that contain a RFID chip so that the absence of the shrink wrap containing the RFID chip indicates that the associated medical supply needs replenishing or is out of compliance with local or federal safety laws and regulations.

BRIEF DESCRIPTION OF THE DRAWINGS

The drawings are only for purposes of illustrating various embodiments and are not to be construed as limiting, wherein.

DETAILED DESCRIPTION OF THE DRAWINGS

Figure 1:
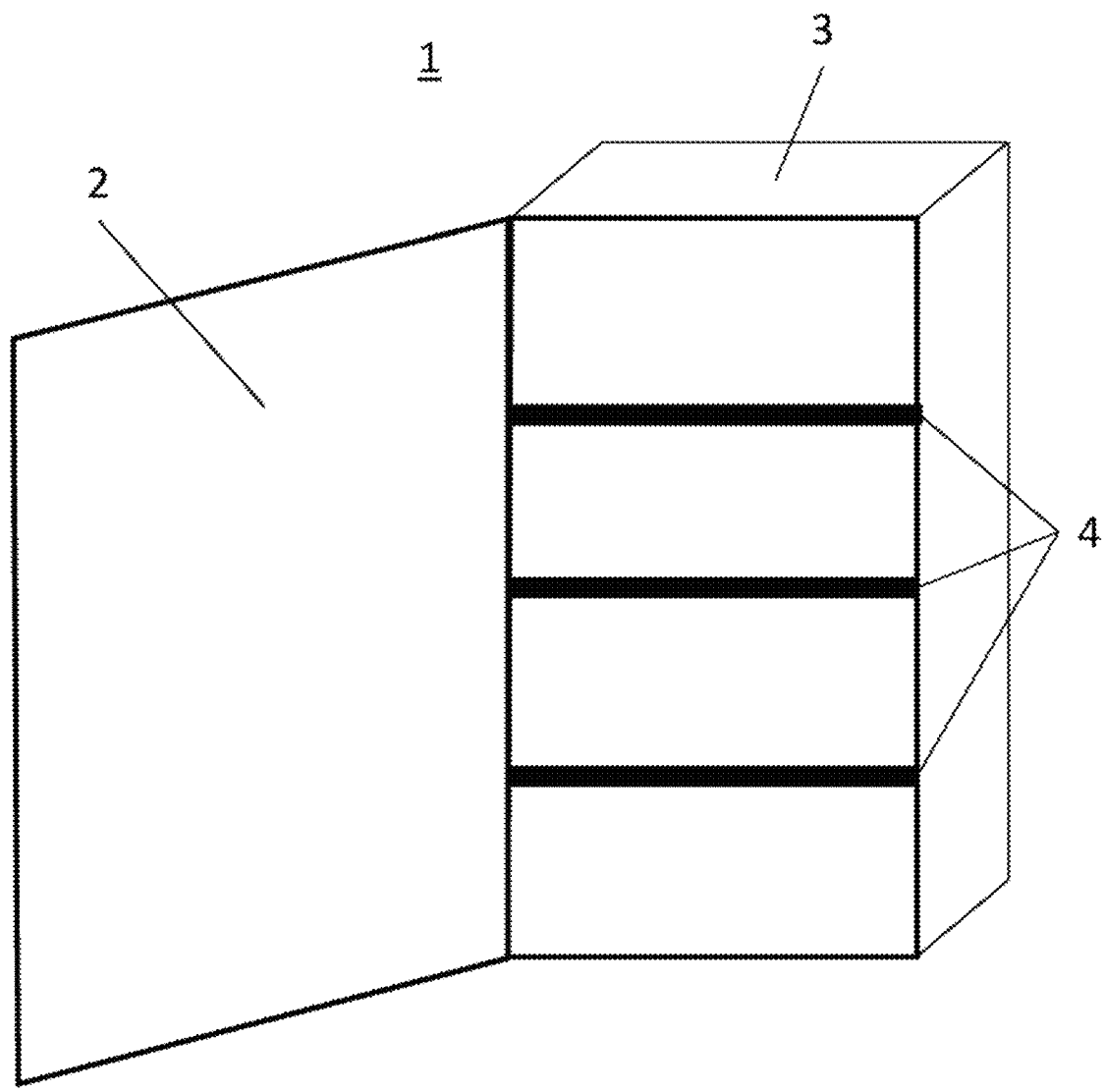
FIG. 1 illustrates a conventional medical supply cabinet.

For a general understanding, reference is made to the drawings. In the drawings, like references have been used throughout to designate identical or equivalent elements. It is also noted that the drawings may not have been drawn to scale and that certain regions may have been purposely drawn disproportionately so that the features and concepts could be properly illustrated.

Figure 2:
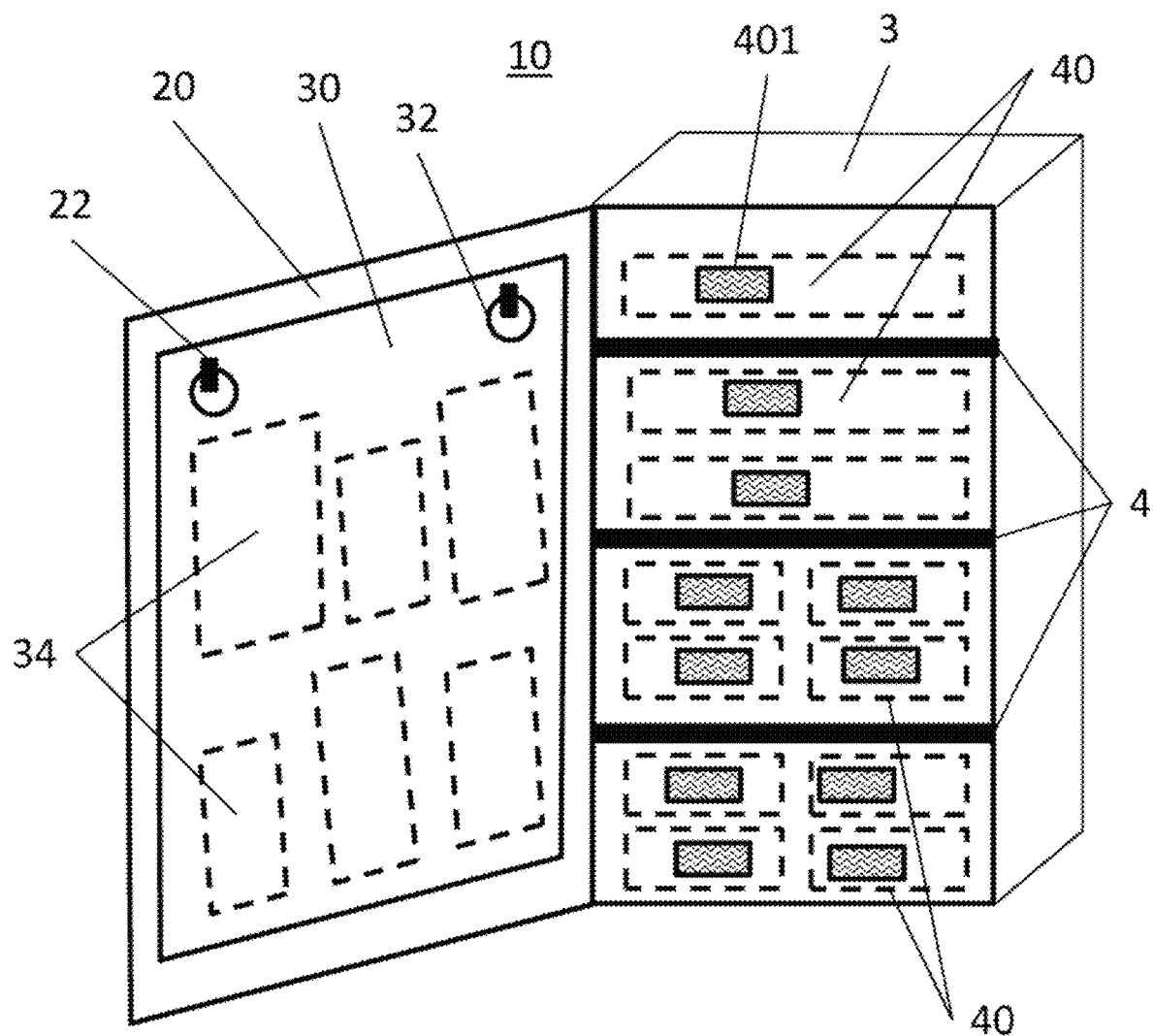
FIG. 2 illustrates an embodiment of a medical supply cabinet.

FIG. 2 illustrates a medical supply cabinet 10 that includes a cabinet storage volume 3 and a door 20. The cabinet storage volume 3 includes various shelves 4, on which medical modules 40 can be placed and stored.

As illustrated in FIG. 2, the medical modules 40 are medical modules, wherein each medical module 40 contains specific medical supplies to address a specific medical situation. For example, the medical modules 40 may be a body fluids clean-up module, a burns module, an eye wound module, a minor wound module, a resuscitation module, a serious wound module, and/or a splint & tourniquet module.

In a preferred embodiment of the medical supply cabinet, each medical module 40 has a predetermined storage location on a predetermined shelf 4. For example, the body fluids clean-up module may have the predetermined storage location of the top shelf 4 of the cabinet storage volume 3.

On the other hand, the serious wound module may have a predetermined storage location of being placed above a splint & tourniquet module on the left side of the bottom of the cabinet storage volume 3, and the burns module may have a predetermined storage location of being placed below an eye wound module on the right side of the first shelf 4 from the bottom of the cabinet storage volume 3.

Each medical module 40 also includes a radio frequency identification (RFID) tag 401 identifying the contents of the associated medical module. The medical supply cabinet 10 may have associated therewith a radio frequency identification (RFID) tag so that when medical supply cabinet 10 is scanned by a radio frequency identification (RFID) tag reader, the appropriate inventory levels can be obtained for comparison purposes with the current inventory levels.

As illustrated in FIG. 2, the medical supply cabinet 10 also includes a removable liner 30 that attaches to the door 20. The door may include hooks 22 that engage openings 32 in the removable liner 30 to enable the attachment of the removable liner 30 to the door 20.

The removable liner 30 includes a plurality of transparent pouches 34 to store medical supplies (not shown). These medical supplies may not be conducive to storage on one of the shelves 4.

For example, the transparent pouches 34 may store triangular bandages, burn gel packets, hand sanitizer packets, gauze pads, low adherent dressing, butterfly closures, instant ice pack, visual fingertip/knuckle bandages, visual strips, visual tape, splinter probes, disposable face shield, finger cot, triple antibiotic ointment, eyewash, antiseptic wipes, forceps, first aid guide pamphlet, and/or scissors.

In a preferred embodiment of the medical supply cabinet, each transparent pouch 34 is configured to store a particular medical supply. For example, the transparent pouch 34, in the upper right corner, may be configured to store the first aid guide pamphlet. On the other hand, the transparent pouch 34, in the lower left corner, may be configured to store the antiseptic wipes.

Figure 3:
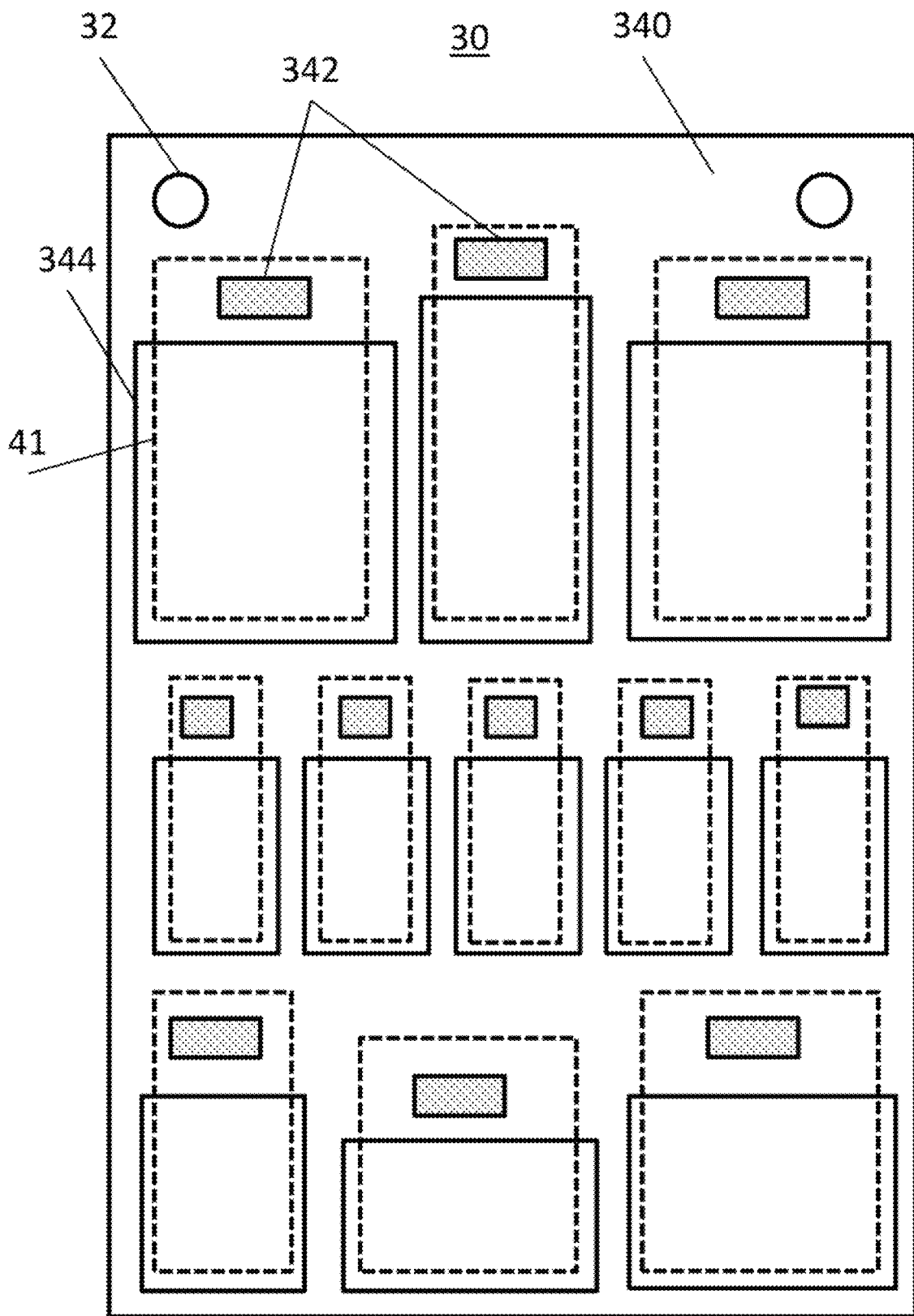
FIG. 3 illustrates an embodiment of a first side of a liner for attachment to a door of the medical supply cabinet of FIGS. 2, 5, and 7.
Figure 5:
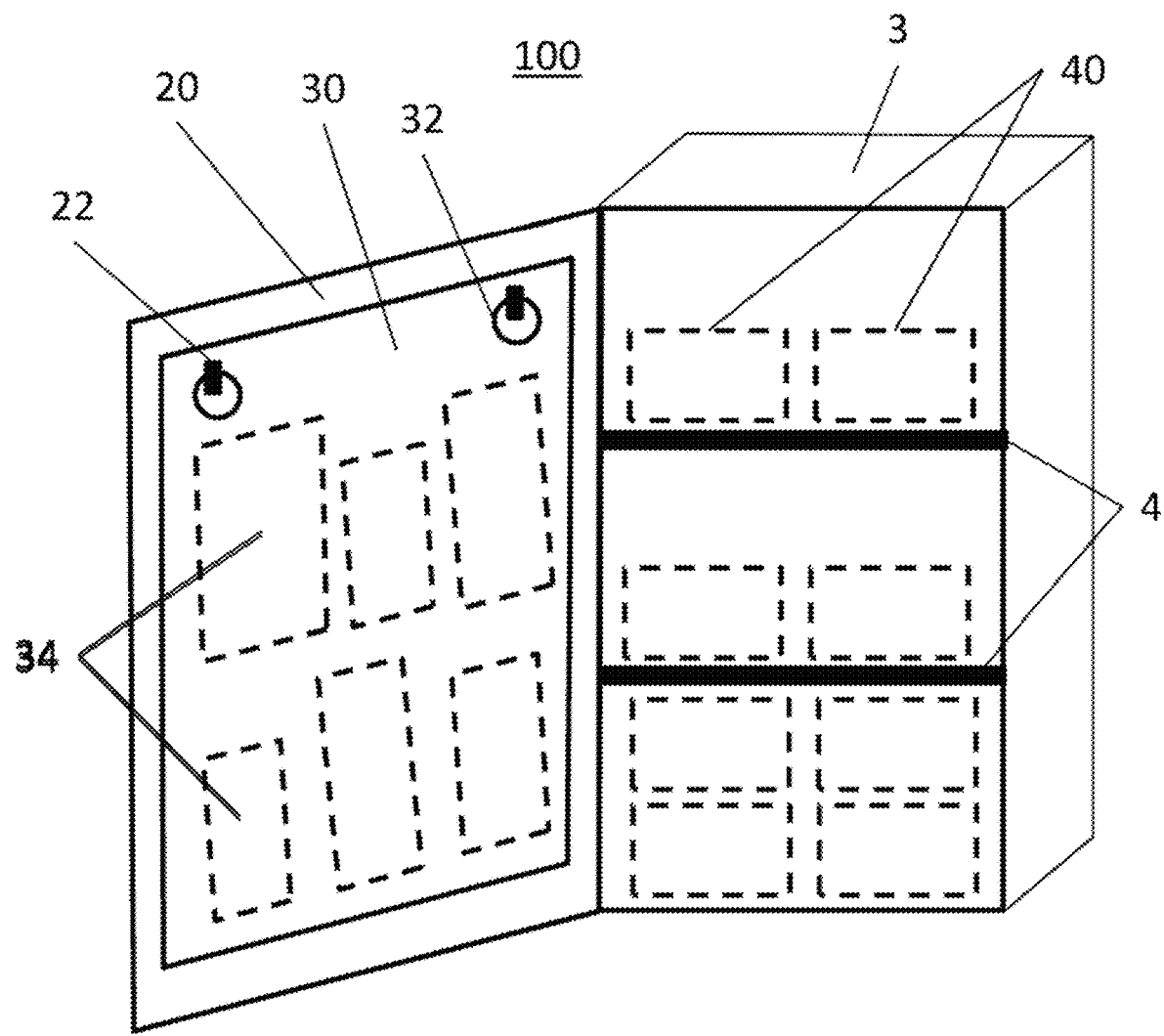
FIG. 5 illustrates another embodiment of a medical supply cabinet.
Figure 7:
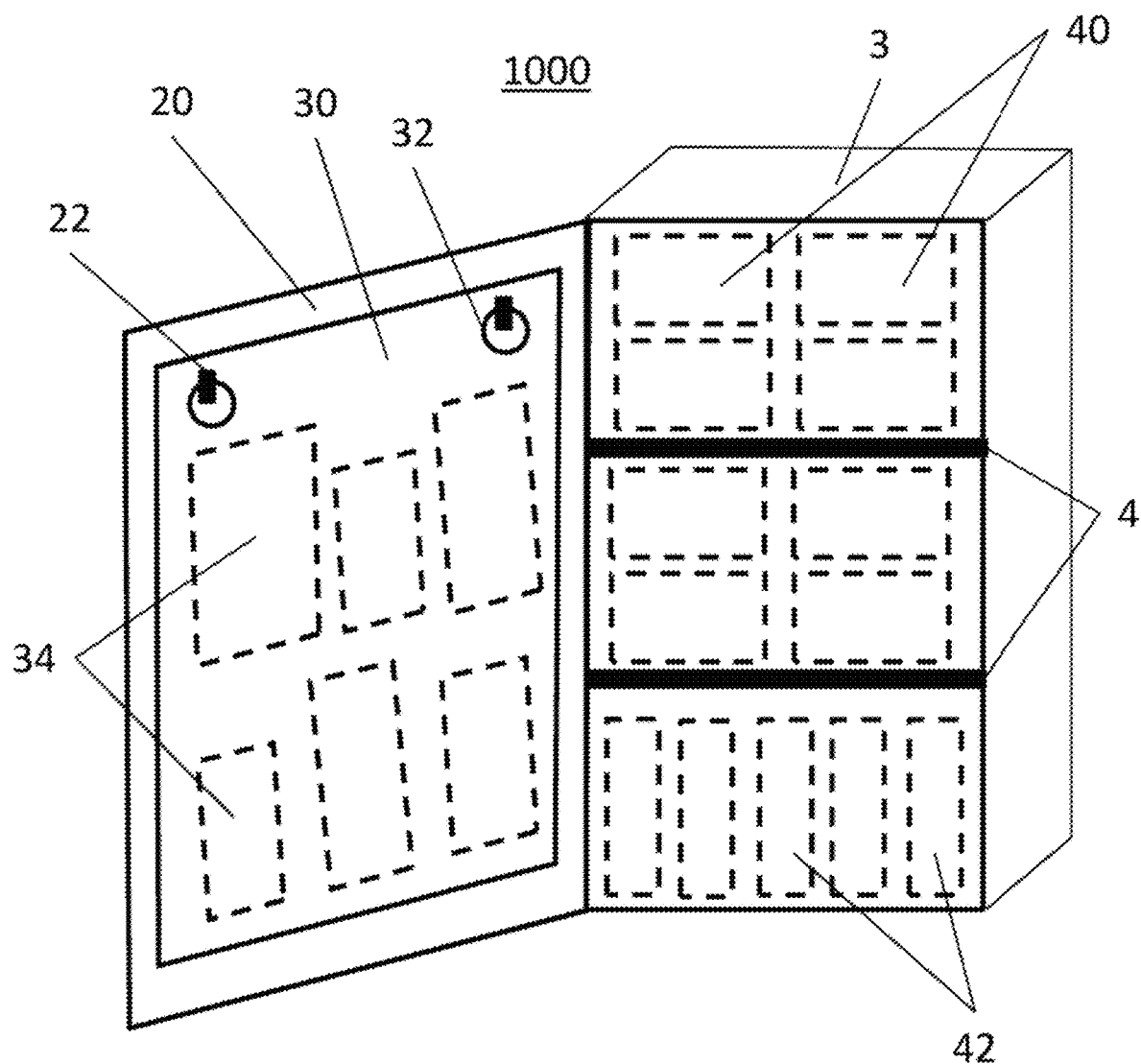
FIG. 7 illustrates the medical supply cabinet of FIG. 5 having a different medical supply configuration.

FIG. 3 illustrates a first side 340 of removable liner 30 for the medical supply cabinets of FIGS. 2, 5, and 7. As illustrated in FIG. 3, the first side 340 of removable liner 30 includes a plurality of transparent pouches 344. Each transparent pouch 344 is configured to store a particular medical supply 41.

Figure 10:
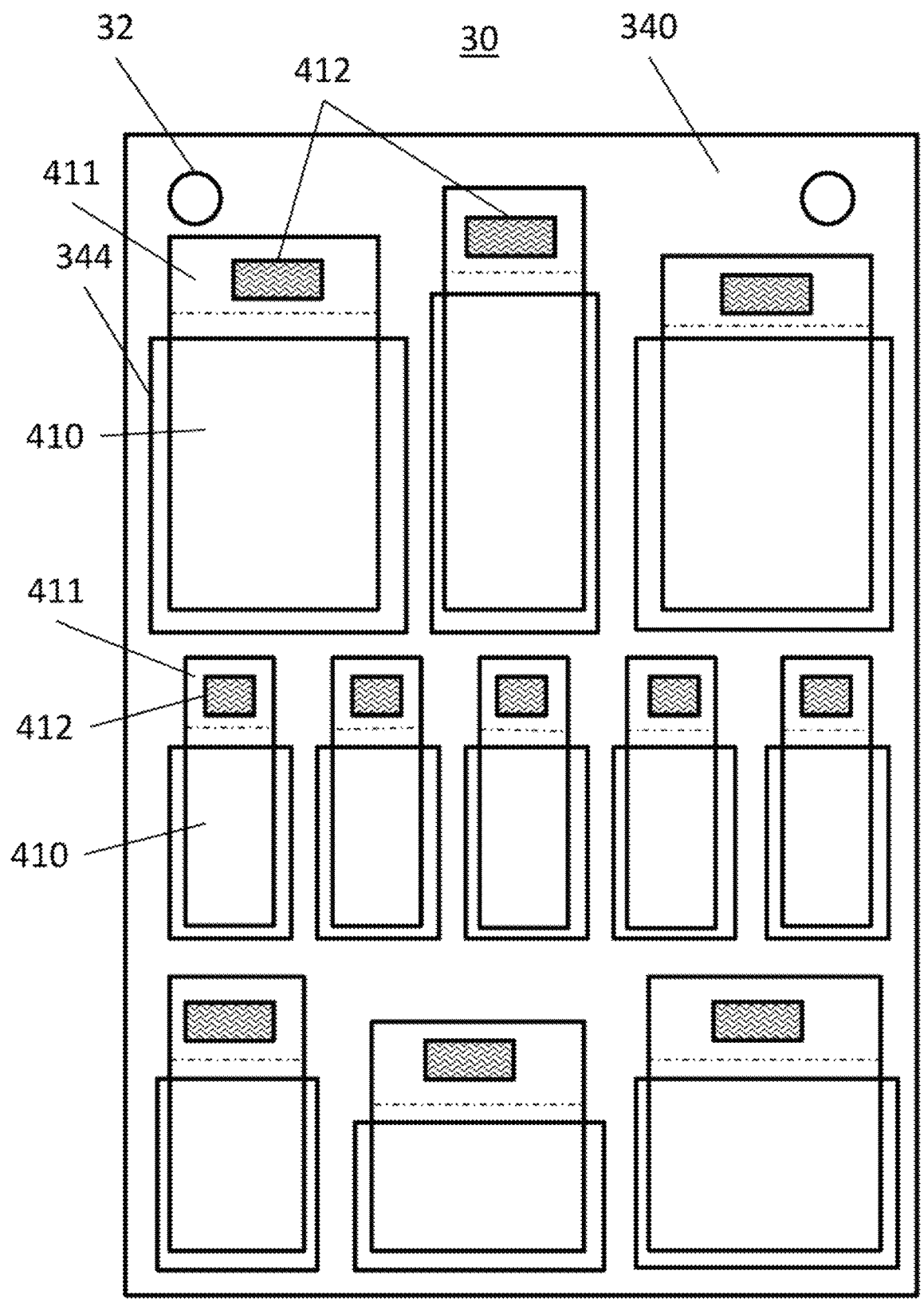
FIG. 10 illustrates a further embodiment of a first side of a liner for attachment to a door of the medical supply cabinet of FIGS. 2, 5, and 7.

As illustrated in FIG. 10, the packaging 410 of each medical supply includes a tear-away portion 411 that is detached from the packaging 410 when a user is accessing the medical supply 41 therein. The tear-away portion 411 includes a radio frequency identification (RFID) tag 412, which identifies the contents of the associated packaging 410 of the medical supply for inventory control purposes.

The medical supply cabinet 10 may have associated therewith a radio frequency identification (RFID) tag reader so that when a tear-away portion 411 is removed from the removable liner 30, the removal of the tear-away portion 411 can be recorded for inventory control purposes.

As further illustrated by FIG. 3, associated with each transparent pouch 344 is a machine readable code or graphic 342, located on the removable liner 30, which represents the particular medical supply 41, for which the transparent pouch 344 was configured.

As illustrated in FIG. 3, the machine readable code or graphic 342 is not visible when the associated medical supply 41 is in the transparent pouch 344. More specifically, the machine readable code or graphic 342 is hidden behind the associated medical supply 41 in the transparent pouch 344 so that machine readable code or graphic 342 cannot be read.

The machine readable code or graphic 342 may be a barcode, glyphs, a QR Code, a Unique Item Identifier code, or a set of symbols or graphical marks, that communicates to a machine (such as a scanner) the identity of the particular medical supply 41 for which the associated transparent pouch 344 was configured.

By utilizing a machine readable code or graphic that requires a visual scanning (such as carried out by a laser driven or light driven scanner) of the machine readable code or graphic 342 to effectively communicate to a machine the identity of the particular medical supply 41 for which the associated transparent pouch 344 was configured, the placement of the machine readable code or graphic 342 to be optically hidden by the medical supply 41 prevents a mistaken reading of the machine readable code or graphic 342 when the associated transparent pouch 344 still contained the particular medical supply 41 for which the associated transparent pouch 344.

Moreover, the machine readable code or graphic 342, and the location thereof, allows the full optical scanning of the first side 340 of removable liner 30 to determine which particular medical supplies 41 need replenishing without manually removing unnecessary scanned information because the relationship between of the location of the machine readable code or graphic 342 and the presence of particular medical supplies 41 effectively filters or blocks the scanning of unnecessary or undesired machine readable codes or graphics 342.

Figure 4:
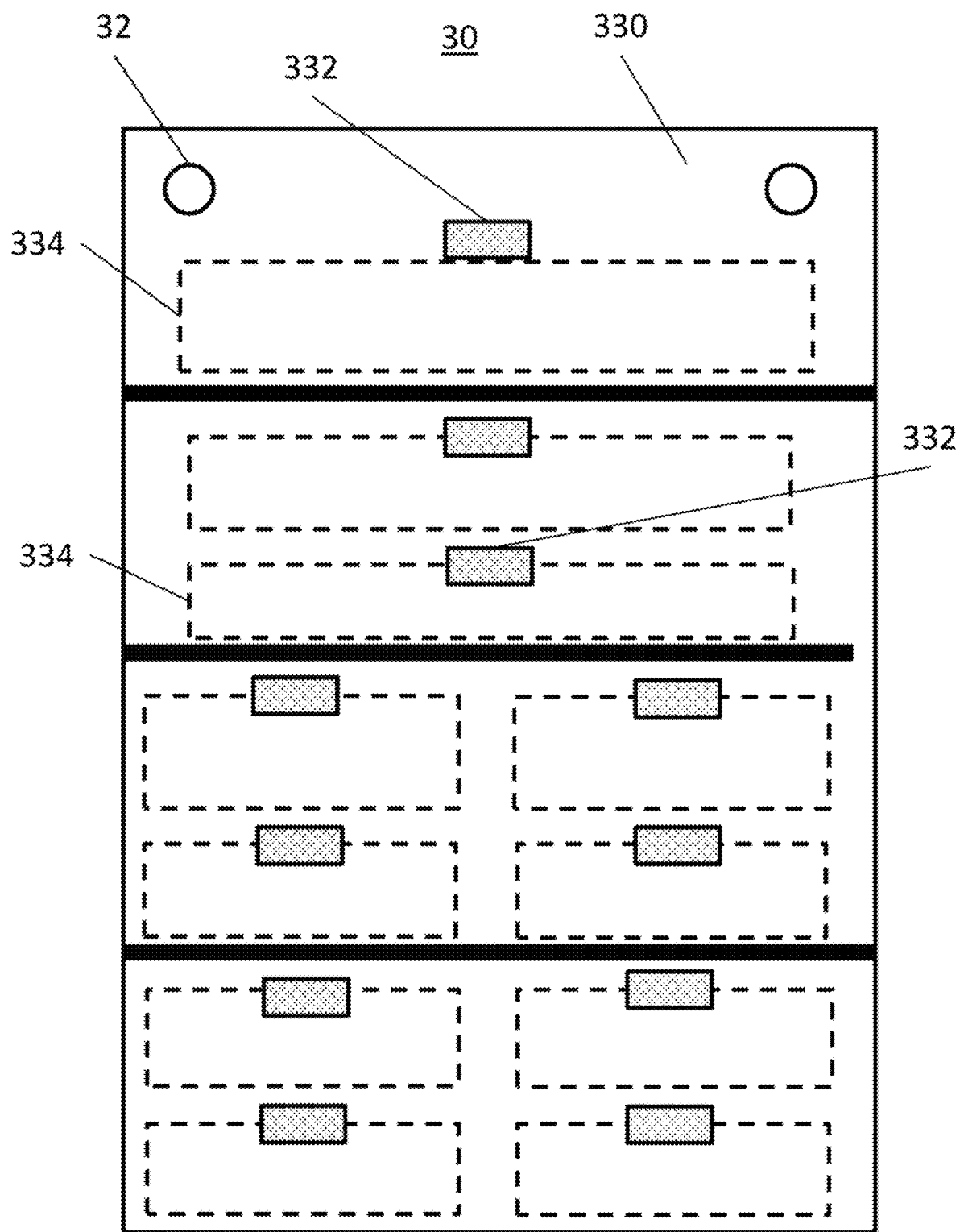
FIG. 4 illustrates a second side of the liner of FIG. 3.

FIG. 4 illustrates a second side 330 of the removable liner 30 for the medical supply cabinets of FIG. 2. As illustrated in FIG. 4, the second side 330 of removable liner 30 includes a plurality of machine readable codes or graphics 332. Each machine readable code or graphic 332 is located on the removable liner 30 so as to represent a location of a particular medical module 40 in the cabinet storage volume 3.

Moreover, each machine readable code or graphic 332 has associated therewith human discernable symbols or graphics to effectively convey the identity of the particular medical module 40 associated therewith.

As illustrated in FIG. 4, when the removable liner 30 is attached to the door 20 so that the second side 330 of the removable liner 30 faces outwardly (away from the door 20), a comparison of the actual inventory of medical modules 40 in the cabinet storage volume 3 with a desired inventory of medical modules 40 in the cabinet storage volume 3 can be readily realized.

Thus, when determining which medical modules 40 need to be replenish, the proper machine readable code or graphic 332 can be scanned by a visual inspection of the second side 330 of the removable liner 30 and the actual inventory of medical modules 40 in the cabinet storage volume 3.

For example, if the body fluids clean-up module is missing from the top shelf 4 of the cabinet storage volume 3, the machine readable code or graphic 332 located at the top of the second side 330 of the removable liner 30 can be scanned to effectively communicate that the medical supply cabinet needs a body fluids clean-up module.

Unlike the first side 340 of the removable liner 30, the second side 330 of the removable liner 30 cannot be fully scanned without manually removing the unnecessary or undesired information from the incorrectly scanned machine readable codes or graphics 332. The second side 330 of the removable liner 30 can be effectively fully scanned if the cabinet storage volume 3 is completely empty.

The machine readable code or graphic 332 may be a barcode, glyphs, a QR Code, a Unique Item Identifier code, or a set of symbols or graphical marks, that communicates to a machine (such as a scanner) the identity of the particular medical module 40.

The machine readable code or graphic 332, and the location thereof, allows the discrete scanning of the second side 330 of removable liner 30 to determine which particular medical modules 40 need replenishing because the relationship between of the location of the machine readable code or graphic 332 and the absence of the particular medical module 40 in the cabinet storage volume 3 effectively communicates to the user of the scanner which machine readable codes or graphics 332 to scan.

FIG. 5 illustrates a medical supply cabinet 100 that includes a cabinet storage volume 3 and a door 20. The cabinet storage volume 3 includes various shelves 4, on which medical modules 40 can be placed and stored.

As illustrated in FIG. 5, the medical modules 40 are medical modules, wherein each medical module 40 contains specific medical supplies to address a specific medical situation. For example, the medical modules 40 may be a body fluids clean-up module, a burns module, an eye wound module, a minor wound module, a resuscitation module, a serious wound module, and/or a splint & tourniquet module.

In a preferred embodiment of the medical supply cabinet, each medical module 40 has a predetermined storage location on a predetermined shelf 4. For example, the body fluids clean-up module may have the predetermined storage location of the left side of the top shelf 4 of the cabinet storage volume 3.

On the other hand, the serious wound module may have a predetermined storage location of being placed above a splint & tourniquet module on the left side of the bottom of the cabinet storage volume 3, and the burns module may have a predetermined storage location of being placed on the right side of the first shelf 4 from the bottom of the cabinet storage volume 3.

As illustrated in FIG. 5, the medical supply cabinet 10 also includes a removable liner 30 that attaches to the door 20. The door may include hooks 22 that engage openings 32 in the removable liner 30 to enable the attachment of the removable liner 30 to the door 20.

The removable liner 30 includes a plurality of transparent pouches 34 to store medical supplies (not shown). These medical supplies may not be conducive to storage on one of the shelves 4.

For example, the transparent pouches 34 may store triangular bandages, burn gel packets, hand sanitizer packets, gauze pads, low adherent dressing, butterfly closures, instant ice pack, visual fingertip/knuckle bandages, visual strips, visual tape, splinter probes, disposable face shield, finger cot, triple antibiotic ointment, eyewash, antiseptic wipes, forceps, first aid guide pamphlet, and/or scissors.

In a preferred embodiment of the medical supply cabinet, each transparent pouch 34 is configured to store a particular medical supply. For example, the transparent pouch 34, in the upper right corner, may be configured to store the first aid guide pamphlet. On the other hand, the transparent pouch 34, in the lower left corner, may be configured to store the antiseptic wipes.

Figure 6:
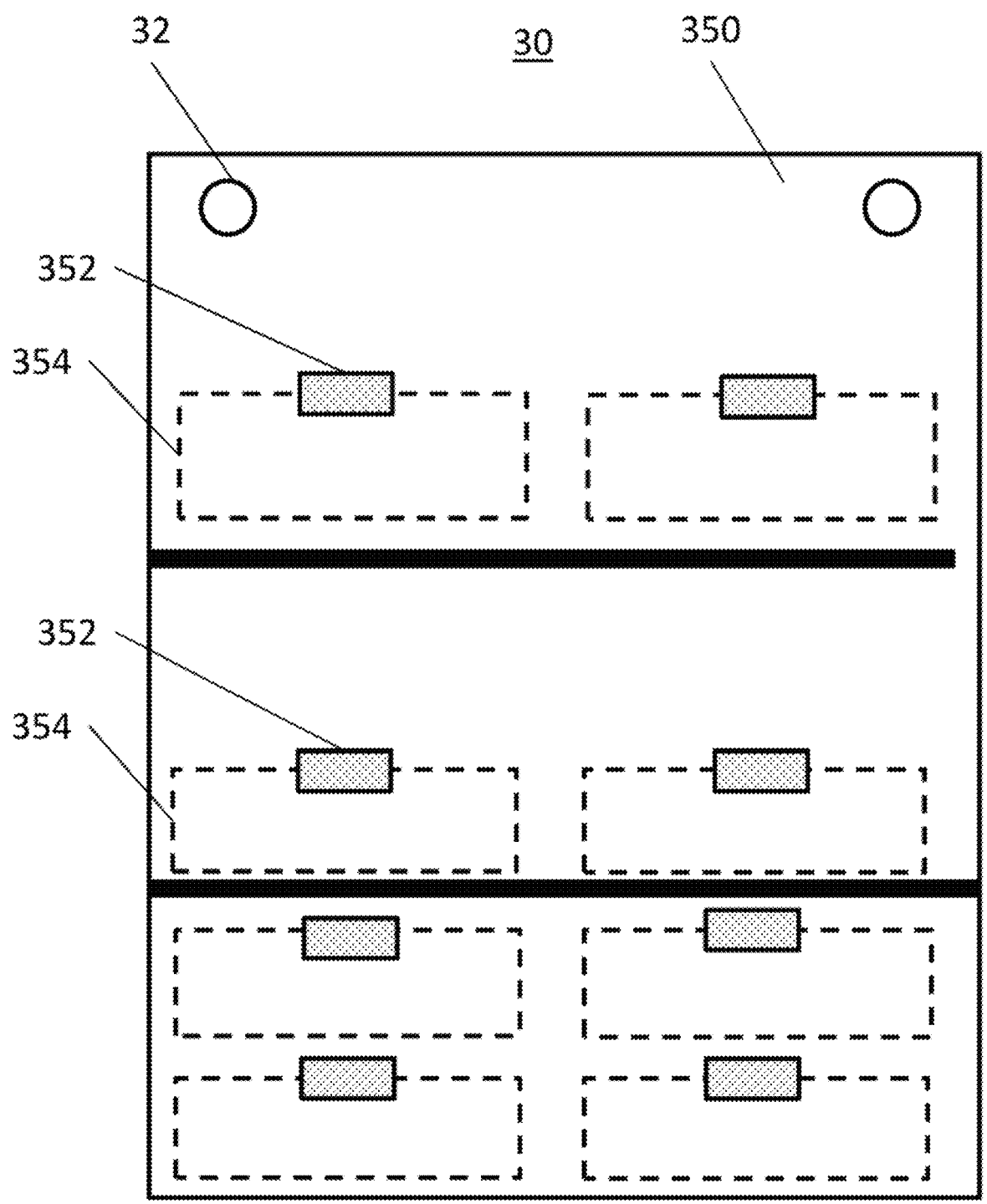
FIG. 6 illustrates an embodiment of a second side of a liner for attachment to a door of the medical supply cabinet of FIG. 5.

FIG. 6 illustrates a second side 350 of the removable liner 30 for the medical supply cabinet of FIG. 5. As illustrated in FIG. 6, the second side 350 of removable liner 30 includes a plurality of machine readable codes or graphics 352. Each machine readable code or graphic 352 is located on the removable liner 30 so as to represent a location of a particular medical module 40 in the cabinet storage volume 3 of FIG. 5.

Moreover, each machine readable code or graphic 352 has associated therewith human discernable symbols or graphics 354 to effectively convey the identity of the particular medical module 40 associated therewith.

As illustrated in FIG. 6, when the removable liner 30 is attached to the door 20 so that the second side 350 of the removable liner 30 faces outwardly (away from the door 20), a comparison of the actual inventory of medical modules 40 in the cabinet storage volume 3 of FIG. 5 with a desired inventory of medical modules 40 in the cabinet storage volume 3 of FIG. 5 can be readily realized.

Thus, when determining which medical modules 40 need to be replenish, the proper machine readable code or graphic 352 can be scanned by a visual inspection of the second side 350 of the removable liner 30 and the actual inventory of medical modules 40 in the cabinet storage volume 3.

For example, if the body fluids clean-up module is missing from the top shelf 4 of the cabinet storage volume 3, the machine readable code or graphic 332 located at the top left of the second side 350 of the removable liner 30 can be scanned to effectively communicate that the medical supply cabinet needs a body fluids clean-up module.

Unlike the first side 340 of the removable liner 30, the second side 350 of the removable liner 30 cannot be fully scanned without manually removing the unnecessary or undesired information from the incorrectly scanned machine readable codes or graphics 352. The second side 350 of the removable liner 30 can be effectively fully scanned if the cabinet storage volume 3 is completely empty.

The machine readable code or graphic 352 may be a barcode, glyphs, a QR Code, a Unique Item Identifier code, or a set of symbols or graphical marks, that communicates to a machine (such as a scanner) the identity of the particular medical module 40.

The machine readable code or graphic 352, and the location thereof, allows the discrete scanning of the second side 350 of removable liner 30 to determine which particular medical modules 40 need replenishing because the relationship between of the location of the machine readable code or graphic 352 and the absence of the particular medical module 40 in the cabinet storage volume 3 effectively communicates to the user of the scanner which machine readable codes or graphics 352 to scan.

FIG. 7 illustrates a medical supply cabinet 1000 that includes a cabinet storage volume 3 and a door 20. The cabinet storage volume 3 includes various shelves 4, on which medical modules 40 can be placed and stored. The cabinet storage volume 3 includes containers of medicine 42 located on the bottom of the cabinet storage volume 3.

As illustrated in FIG. 7, the medical modules 40 are medical modules, wherein each medical module 40 contains specific medical supplies to address a specific medical situation. For example, the medical modules 40 may be a body fluids clean-up module, a burns module, an eye wound module, a minor wound module, a resuscitation module, a serious wound module, and/or a splint & tourniquet module.

Each container of medicine 42 contains a specific medicine. For example, a container of medicine 42 may contain pain reliever, ibuprofen, non-aspirin, cold relief, and/or antacid.

In a preferred embodiment of the medical supply cabinet, each medical module 40 has a predetermined storage location on a predetermined shelf 4. For example, the body fluids clean-up module may have the predetermined storage location above a splint & tourniquet module on the left side of the top shelf 4 of the cabinet storage volume 3. On the other hand, the serious wound module may have a predetermined storage location of being placed above a minor module on the right side of the first shelf 4 from the bottom of the cabinet storage volume 3.

On the bottom of the cabinet storage volume 3, each container of medicine 42 has a predetermined storage location. For example, a pain reliever container may be located on the left side of bottom of the cabinet storage volume 3.

As illustrated in FIG. 7, the medical supply cabinet 10 also includes a removable liner 30 that attaches to the door 20. The door may include hooks 22 that engage openings 32 in the removable liner 30 to enable the attachment of the removable liner 30 to the door 20.

The removable liner 30 includes a plurality of transparent pouches 34 to store medical supplies (not shown). These medical supplies may not be conducive to storage on one of the shelves 4.

For example, the transparent pouches 34 may store triangular bandages, burn gel packets, hand sanitizer packets, gauze pads, low adherent dressing, butterfly closures, instant ice pack, visual fingertip/knuckle bandages, visual strips, visual tape, splinter probes, disposable face shield, finger cot, triple antibiotic ointment, eyewash, antiseptic wipes, forceps, first aid guide pamphlet, and/or scissors.

In a preferred embodiment of the medical supply cabinet, each transparent pouch 34 is configured to store a particular medical supply. For example, the transparent pouch 34, in the upper right corner, may be configured to store the first aid guide pamphlet. On the other hand, the transparent pouch 34, in the lower left corner, may be configured to store the antiseptic wipes.

Figure 8:
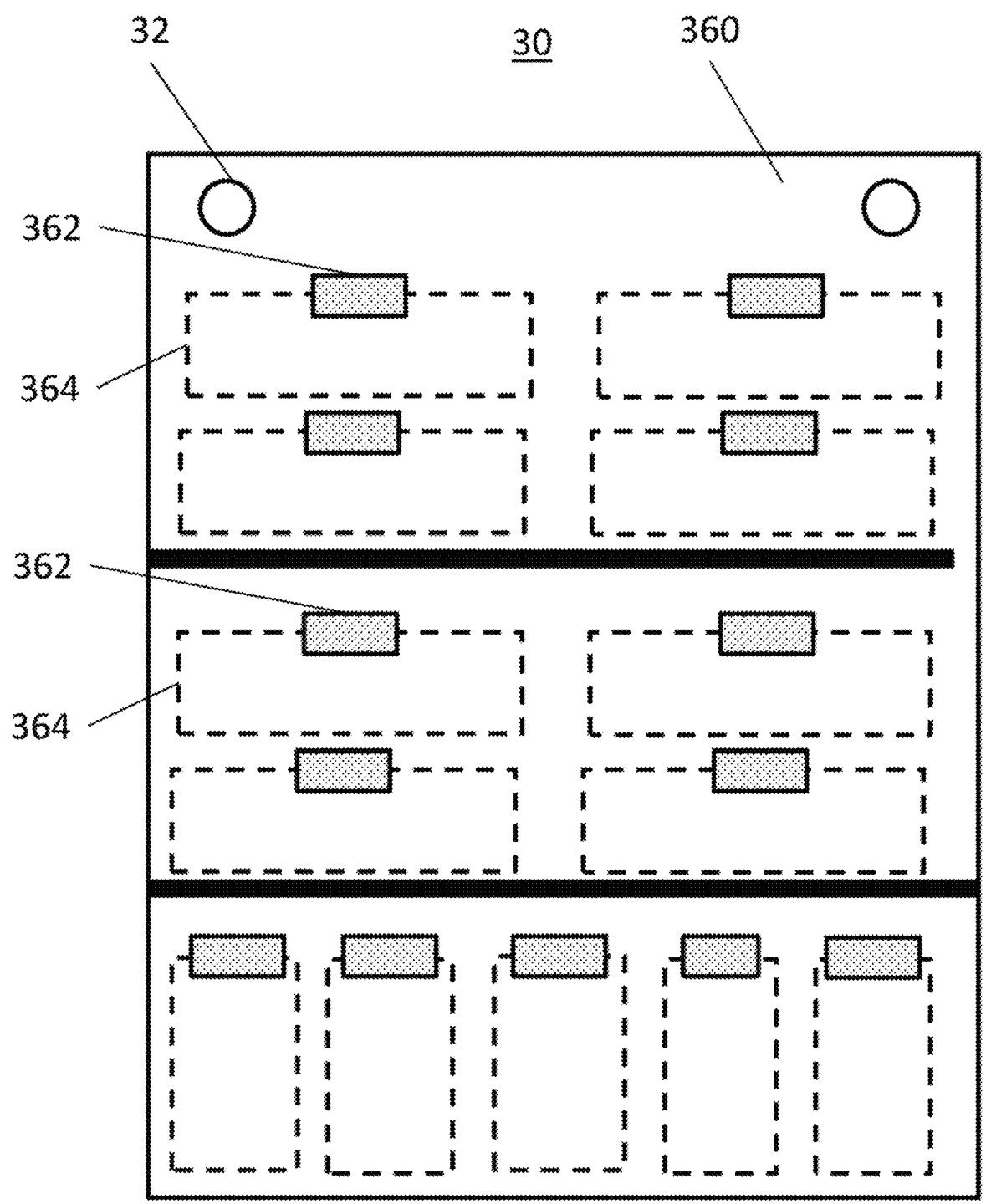
FIG. 8 illustrates an embodiment of a second side of a liner for attachment to a door of the medical supply cabinet of FIG. 7.

FIG. 8 illustrates a second side 360 of the removable liner 30 for the medical supply cabinet of FIG. 7. As illustrated in FIG. 8, the second side 360 of removable liner 30 includes a plurality of machine readable codes or graphics 362. Each machine readable code or graphic 362 is located on the removable liner 30 so as to represent a location of a particular medical module 40 and a container of medicine 42 in the cabinet storage volume 3 of FIG. 7.

Moreover, each machine readable code or graphic 362 has associated therewith human discernable symbols or graphics 364 to effectively convey the identity of the particular medical module 40 associated therewith.

As illustrated in FIG. 8, when the removable liner 30 is attached to the door 20 so that the second side 360 of the removable liner 30 faces outwardly (away from the door 20), a comparison of the actual inventory of medical modules 40 in the cabinet storage volume 3 of FIG. 7 with a desired inventory of medical modules 40 in the cabinet storage volume 3 of FIG. 7 can be readily realized.

Thus, when determining which medical modules 40 need to be replenish, the proper machine readable code or graphic 362 can be scanned by a visual inspection of the second side 360 of the removable liner 30 and the actual inventory of medical modules 40 in the cabinet storage volume 3.

For example, if the body fluids clean-up module is missing from the top shelf 4 of the cabinet storage volume 3, the machine readable code or graphic 362 located at the top left of the second side 360 of the removable liner 30 can be scanned to effectively communicate that the medical supply cabinet needs a body fluids clean-up module.

Unlike the first side 340 of the removable liner 30, the second side 360 of the removable liner 30 cannot be fully scanned without manually removing the unnecessary or undesired information from the incorrectly scanned machine readable codes or graphics 362. The second side 360 of the removable liner 30 can be effectively fully scanned if the cabinet storage volume 3 is completely empty.

The machine readable code or graphic 362 may be a barcode, glyphs, a QR Code, a Unique Item Identifier code, or a set of symbols or graphical marks, that communicates to a machine (such as a scanner) the identity of the particular medical module 40.

The machine readable code or graphic 362, and the location thereof, allows the discrete scanning of the second side 360 of removable liner 30 to determine which particular medical modules 40 need replenishing because the relationship between of the location of the machine readable code or graphic 362 and the absence of the particular medical module 40 in the cabinet storage volume 3 effectively communicates to the user of the scanner which machine readable codes or graphics 362 to scan.

Figure 9:
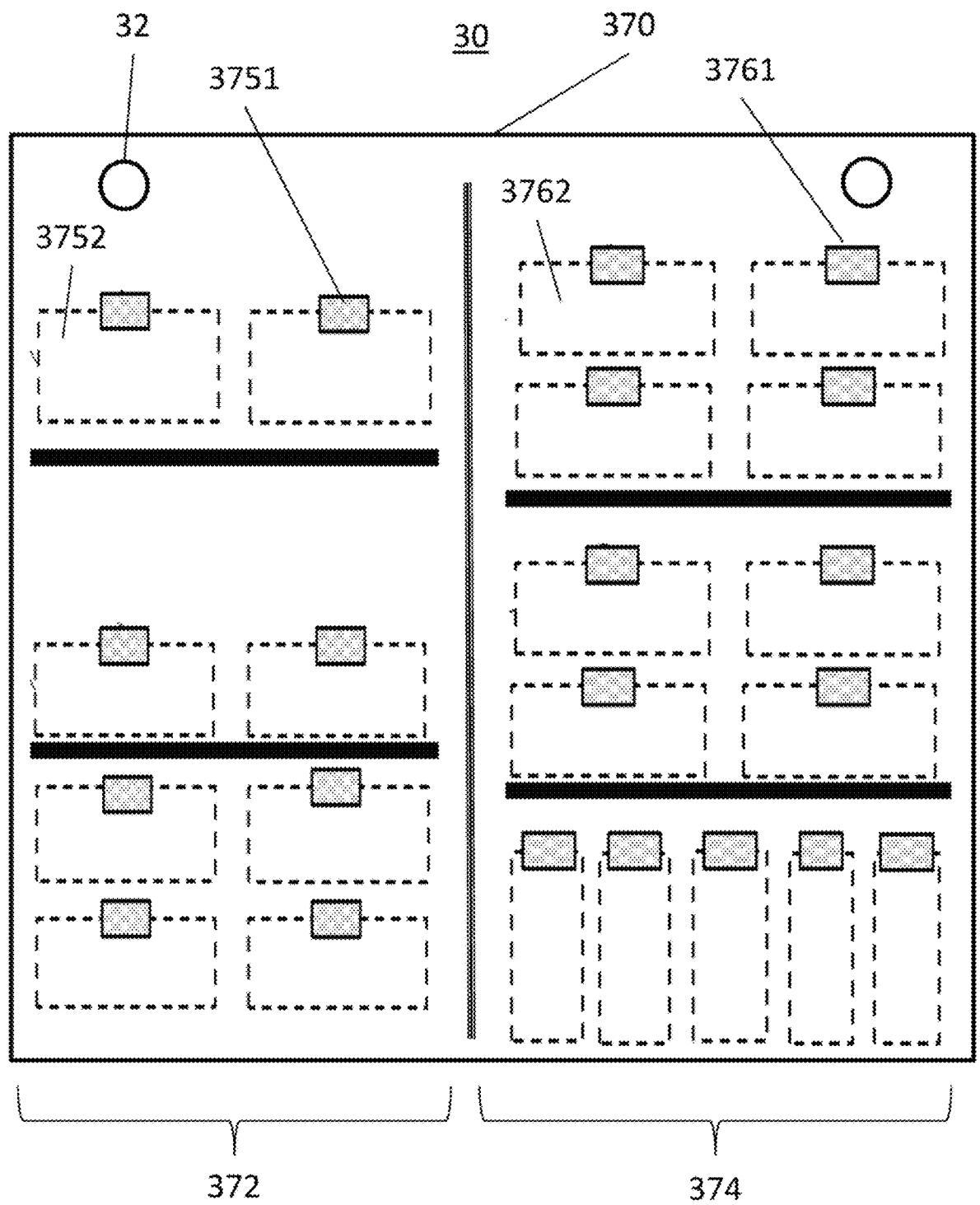
FIG. 9 illustrates an embodiment of a second side of a liner for attachment to a door of either the medical supply cabinet of FIG. 5 or the medical supply cabinet of FIG. 7.

FIG. 9 illustrates a second side 370 of the removable liner 30 for both the medical supply cabinet of FIG. 5 and the medical supply cabinet of FIG. 7. As illustrated in FIG. 9, on one side (left side) of the second side 370 of removable liner 30 includes a plurality of machine readable codes or graphics 3751 and on the other side (right side) of the second side 370 of removable liner 30 includes a plurality of machine readable codes or graphics 3761.

Each machine readable code or graphic 3761 is located on the removable liner 30 so as to represent a location of a particular medical module 40 and a container of medicine 42 in the cabinet storage volume 3 of FIG. 7.

Each machine readable code or graphic 3751 is located on the removable liner 30 so as to represent a location of a particular medical module 40 in the cabinet storage volume 3 of FIG. 5.

Moreover, each machine readable code or graphic 3761 has associated therewith human discernable symbols or graphics 3762 to effectively convey the identity of the particular medical module 40 or container of medicine 42 associated therewith.

Each machine readable code or graphic 3751 has associated therewith human discernable symbols or graphics 3752 to effectively convey the identity of the particular medical module 40 associated therewith.

As illustrated in FIG. 9, when the removable liner 30 is attached to the door 20 so that the second side 370 of the removable liner 30 faces outwardly (away from the door 20), a comparison of the actual inventory of medical modules 40 in the cabinet storage volume 3 of FIG. 7 or the actual inventory of medical modules 40 in the cabinet storage volume 3 of FIG. 5 with a desired inventory of medical modules 40 in the cabinet storage volume 3 of FIG. 7 or a desired inventory of medical modules 40 in the cabinet storage volume 3 of FIG. 5 can be readily realized.

Thus, when determining which medical modules 40 need to be replenish, the proper machine readable code or graphic (3751 or 3761) can be scanned by a visual inspection of the second side 370 of the removable liner 30 and the actual inventory of medical modules 40 (and/or containers of medicine 42) in the appropriate cabinet storage volume 3.

For example, if the body fluids clean-up module is missing from the top shelf 4 of the cabinet storage volume 3 of FIG. 5, the machine readable code or graphic 3752 located at the top left of the second side 370 of the removable liner 30 can be scanned to effectively communicate that the medical supply cabinet needs a body fluids clean-up module.

Unlike the first side 340 of the removable liner 30, the second side 370 of the removable liner 30 cannot be fully scanned without manually removing the unnecessary or undesired information from the incorrectly scanned machine readable codes or graphics (3751 or 3761).

The machine readable code or graphic (3751 or 3761) may be a barcode, glyphs, a QR Code, a Unique Item Identifier code, or a set of symbols or graphical marks, that communicates to a machine (such as a scanner) the identity of the particular medical module 40 and/or container of medicine 42.

The machine readable code or graphic (3751 or 3761), and the location thereof, allows the discrete scanning of the second side 370 of removable liner 30 to determine which particular medical modules 40 and/or containers of medicine 42 need replenishing because the relationship between of the location of the machine readable code or graphic (3751 or 3761) and the absence of the particular medical module 40 and/or containers of medicine 42 in the cabinet storage volume 3 effectively communicates to the user of the scanner which machine readable codes or graphics (3751 or 3761) to scan.

As described above, the removable liner and associated visually machine readable codes or graphics allows the conventional medical supply cabinet to not only increase the amount of supplies contained therein, but enables an accurate replenishing of the used medical supplies.

By exposing the visually machine readable codes or graphics after the medical supply on the removable liner is used (the packaging for the medical supply is discarded), a user can use a machine readable code scanner to accurately identify, even though the packaging of the depleted medical supply is no longer in the transparent pouch, which medical supplies have been depleted and need replenishing.

As an enhancement to this system, the inclusion of RFID tags in the tear away portion of the packaging can also assist in monitoring inventory by recording the use of the medical supplies for inventory control purposes.

However, the use of a RFID tag requires the user of the medical supply to actively scan the tear-away portion of the packaging. In emergency situations, there may not be time to scan the tear-away portion of the packaging or the tear-away portion of the packaging is discarded before a scanning can take place. Thus, the inclusion of the associated visually machine readable codes or graphics on the removable liner provides a redundant (fail-safe) mechanism to enable an accurate identification of which medical supplies have been depleted and need replenishing.

As illustrated in FIG. 10, the medical cabinet liner 30 includes a plurality of pouches 344, wherein each pouch holds medical supply packaging 410, which contains a medical supply. Each medical supply packaging 410 includes a tear away portion 411 that includes a radio frequency identification (RFID) tag 412. When a user removes the medical supply packaging 410 from the pouch 344 and opens the medical supply packaging 410, the tear away portion 411, which includes a radio frequency identification (RFID) tag 412, is thrown away. The removal or discarding of the tear away portion 411, which includes the radio frequency identification (RFID) tag 412, prevents the radio frequency identification (RFID) tag 412 from being read when the medical supply cabinet is scanned by a radio frequency identification (RFID) tag reader for inventory purposes.

In other words, the removal or discarding of the tear away portion 411, which includes the radio frequency identification (RFID) tag 412, informs the inventory system and/or user that the particular medical supply, associated with the removed or discarded radio frequency identification (RFID) tag 412, is either depleted or the remaining amount is less than that required by the client and/or local regulations.

Figure 11:
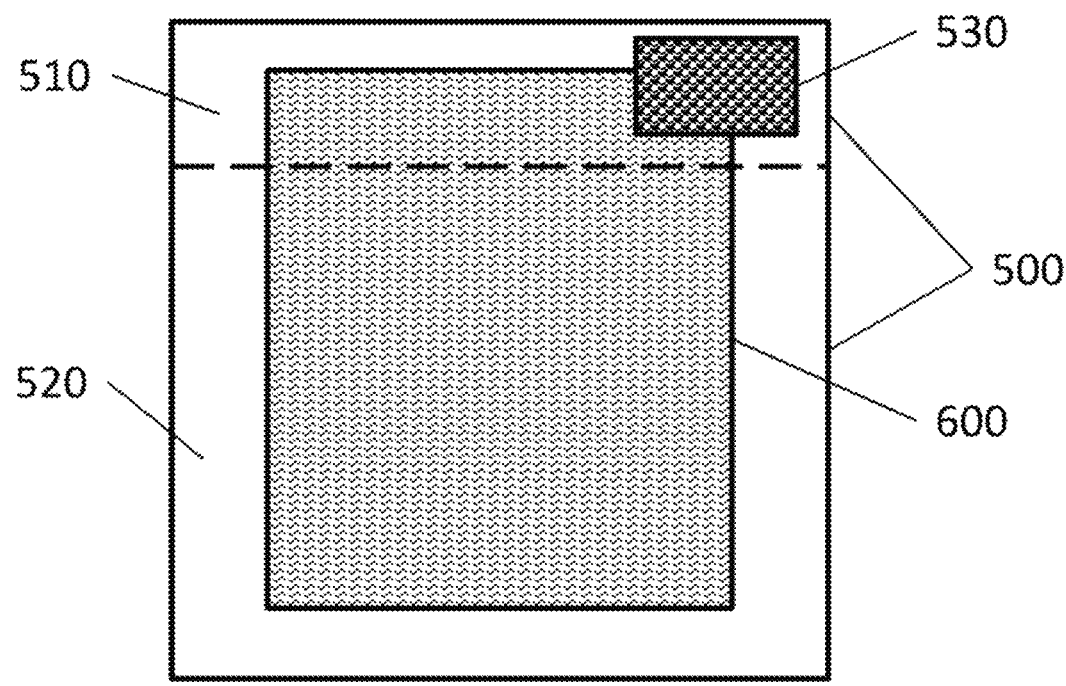
FIG. 11 illustrates medical supply packaging with a tear away radio frequency identification tag.

FIG. 11 illustrates medical supply packaging, which contains a medical supply and a radio frequency identification (RFID) tag. As illustrated in FIG. 11, medical supply packaging 500 is constructed of a tear away portion 510 and a base portion 520. The tear away portion 510 is connected to the base portion 520 via a perforation or other binding configuration that allows for the easy tearing away of the tear away portion 510 from the base portion 520.

The medical supply packaging 500 includes a particular medical supply 600 contained therein. The medical supply packaging 500 also includes a radio frequency identification (RFID) tag 530, located in the tear away portion 510. The radio frequency identification (RFID) tag 530 identifies the particular medical supply 600 contained in the medical supply packaging 500.

As noted above, when a user opens the medical supply packaging 500, the tear away portion 510, which includes a radio frequency identification (RFID) tag 530, is thrown away. The removal or discarding of the tear away portion 510, which includes the radio frequency identification (RFID) tag 530, prevents the radio frequency identification (RFID) tag 530 from being read when the medical supply cabinet is scanned by a radio frequency identification (RFID) tag reader for inventory purposes.

In other words, the removal or discarding of the tear away portion 510, which includes the radio frequency identification (RFID) tag 530, informs the inventory system and/or user that the particular medical supply, associated with the removed or discarded radio frequency identification (RFID) tag 530, is either depleted or the remaining amount is less than that required by the client and/or local regulations.

Figure 12:
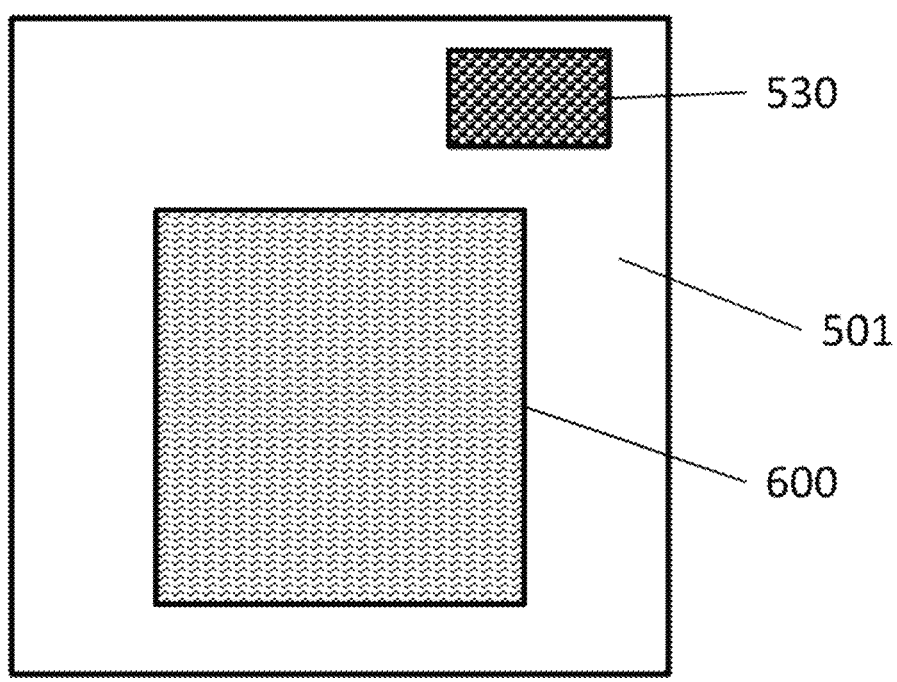
FIG. 12 illustrates medical supply packaging shrink warp with a radio frequency identification tag.

FIG. 12 illustrates medical supply packaging shrink wrap, which contains a medical supply and a radio frequency identification (RFID) tag. As illustrated in FIG. 12, medical supply packaging shrink wrap 501 includes a particular medical supply 600 contained therein. The medical supply packaging shrink wrap 501 also includes a radio frequency identification (RFID) tag 530. The radio frequency identification (RFID) tag 530 identifies the particular medical supply 600 contained in the medical supply packaging shrink wrap 501.

When a user opens the medical supply packaging shrink wrap 501, the medical supply packaging shrink wrap 501, which includes the radio frequency identification (RFID) tag 530, is thrown away. The discarding of the radio frequency identification (RFID) tag 530 prevents the radio frequency identification (RFID) tag 530 from being read when the medical supply cabinet is scanned by a radio frequency identification (RFID) tag reader for inventory purposes.

In other words, the discarding of the radio frequency identification (RFID) tag 530 informs the inventory system and/or user that the particular medical supply, associated with the removed or discarded radio frequency identification (RFID) tag 530, is either depleted or the remaining amount is less than that required by the client and/or local regulations.

Figure 13:
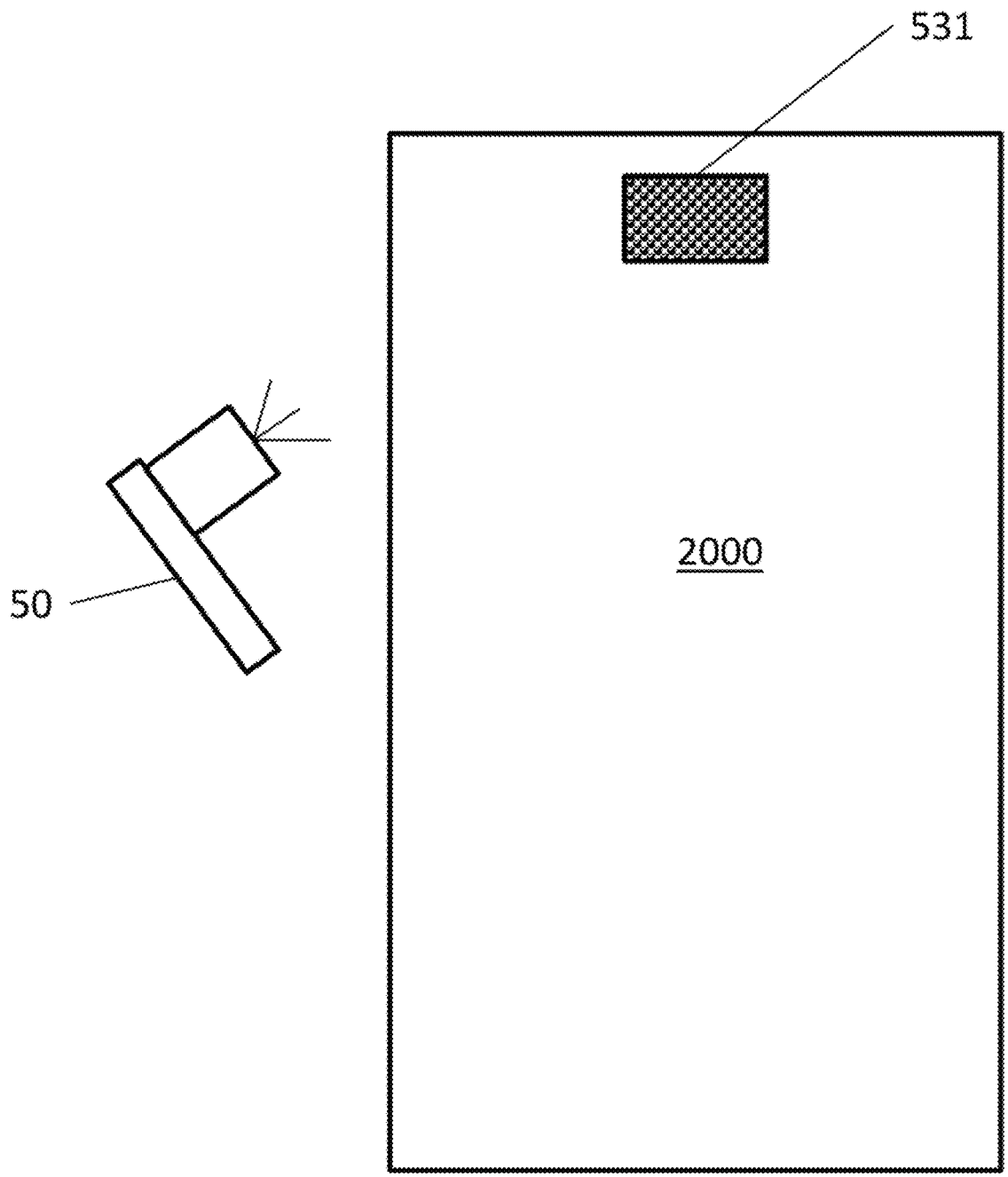
FIG. 13 illustrates a medical supply cabinet with a radio frequency identification tag.

FIG. 13 illustrates the scanning of medical supply cabinet with a radio frequency identification (RFID) tag reader. As illustrated in FIG. 13, a medical supply cabinet 2000 includes a radio frequency identification (RFID) tag 531, which identifies the particular medical supply cabinet so that the list of required medical supplies can be retrieved for comparison with the actual medical supplies in medical supply cabinet 2000 when the medical supply cabinet 2000 is scanned by a radio frequency identification (RFID) tag reader 50. The radio frequency identification (RFID) tag 531 may be located on the outside of the medical supply cabinet 2000 or any other location that is readily scannable by the radio frequency identification (RFID) tag reader 50.

Figure 14:
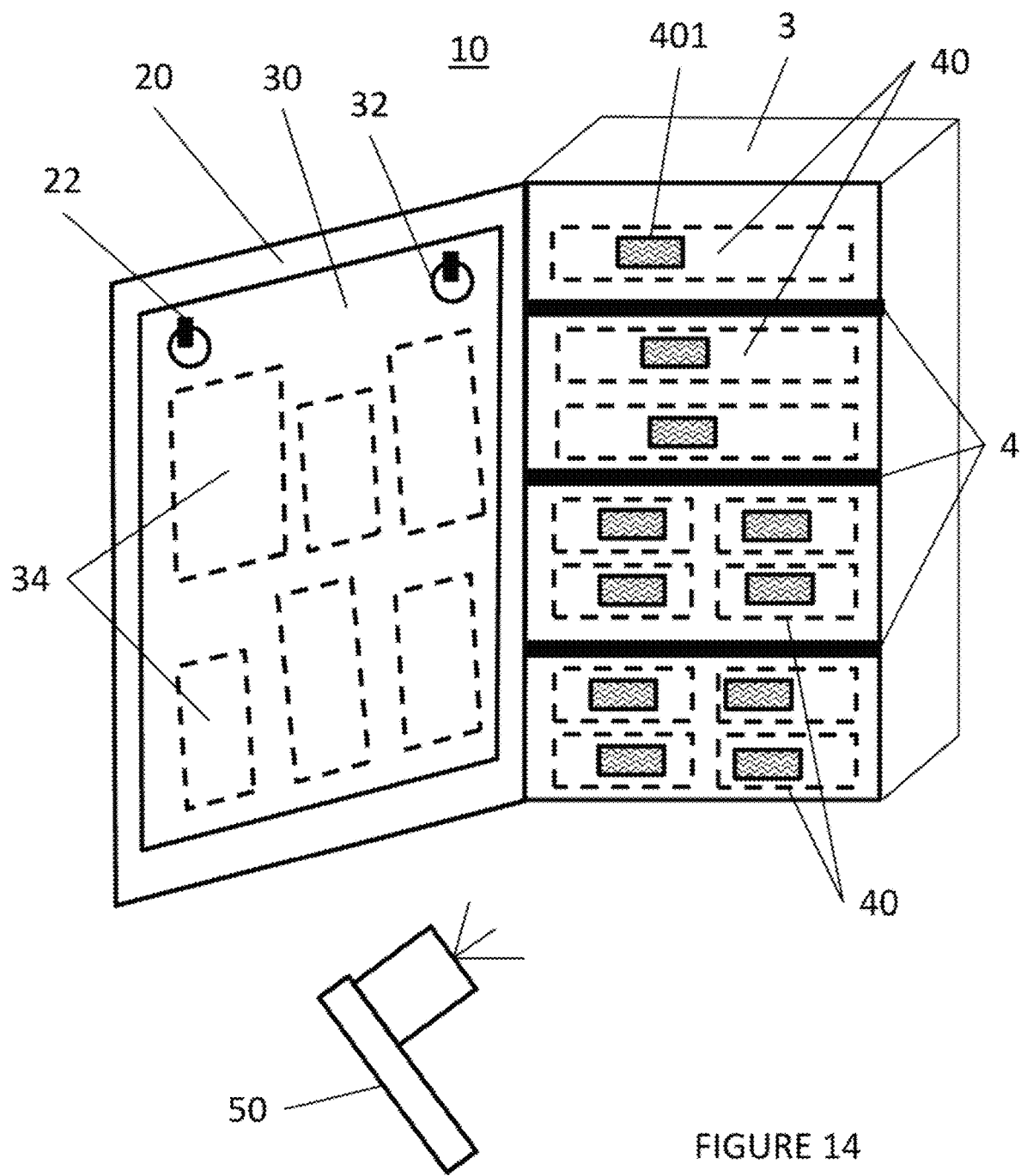
FIG. 14 illustrates a medical supply cabinet with medical modules having radio frequency identification tags.

FIG. 14 illustrates the scanning of the contents of a medical supply cabinet. As illustrated in FIG. 14, a medical supply cabinet 10 includes a plurality of medical supplies or modules 40, wherein each medical supply or module 40 includes a radio frequency identification (RFID) tag 401, which identifies the particular medical supply or module. When of the contents of the medical supply cabinet 10 is scanned by a radio frequency identification (RFID) tag reader 50, the radio frequency identification (RFID) tag reader 50 ascertain which medical supplies or modules 40 are present in the medical supply cabinet 10. This information can be compared to the required medical supplies for the particular medical supply cabinet 10 to determine medical supply deficiencies.

Figure 15:
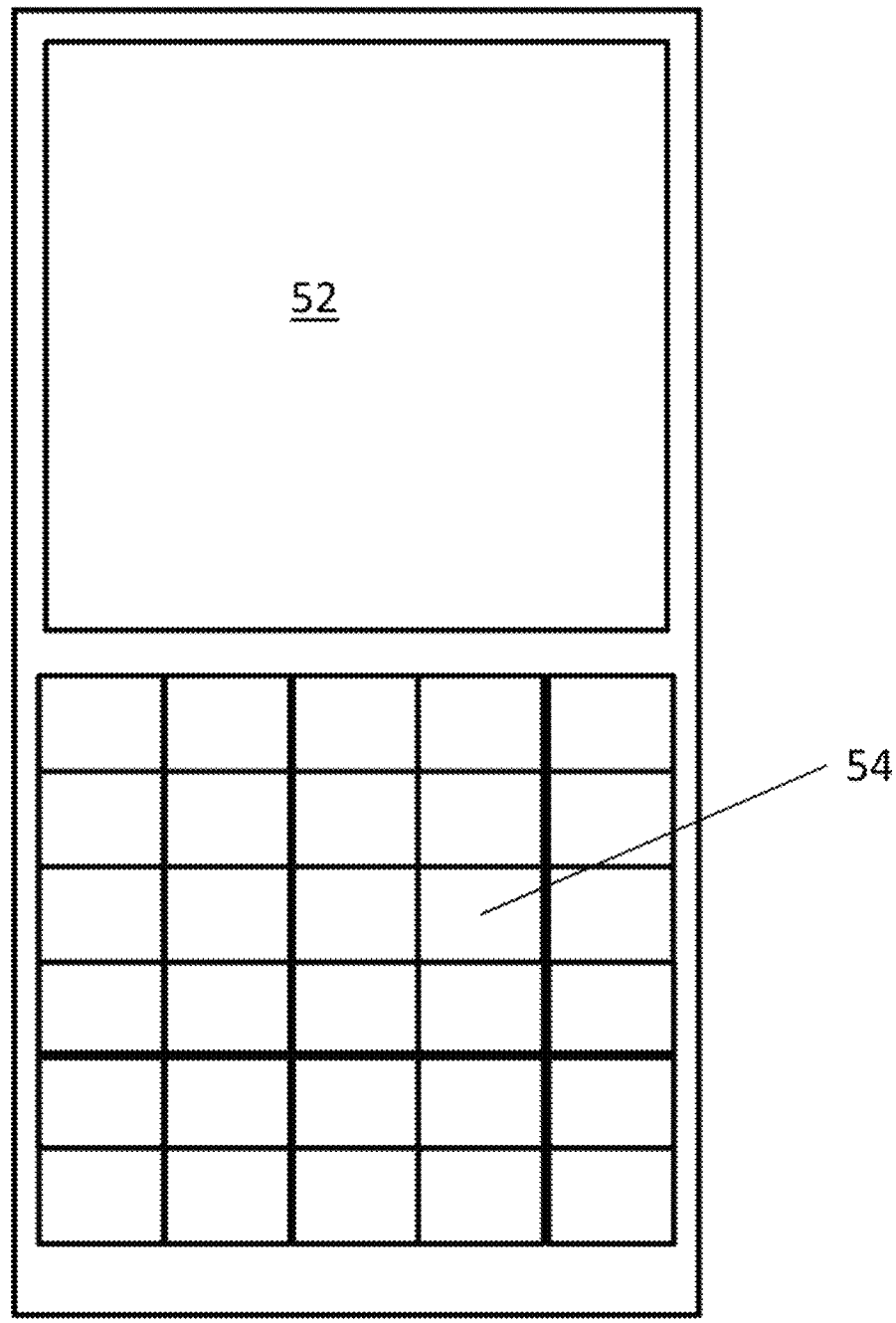
FIG. 15 illustrates an interface device for a radio frequency identification tag reader.

FIG. 15 illustrates an interface device 5000 for a radio frequency identification tag reader. The interface device 5000 includes a display 52 to display information about the medical supply cabinet, such as the scanned contents of the medical supply cabinet and/or the deficiencies of the medical supply cabinet. The interface device 5000 includes an input interface 54, such as a keypad, to enable a user to input information and/or instructions to interface device 5000. It is noted that the display 52 and the input interface 54 may be combined as a touchscreen. Moreover, the interface device 5000 may include a combination of a touchscreen, a display, and/or an input interface.

Figure 16:
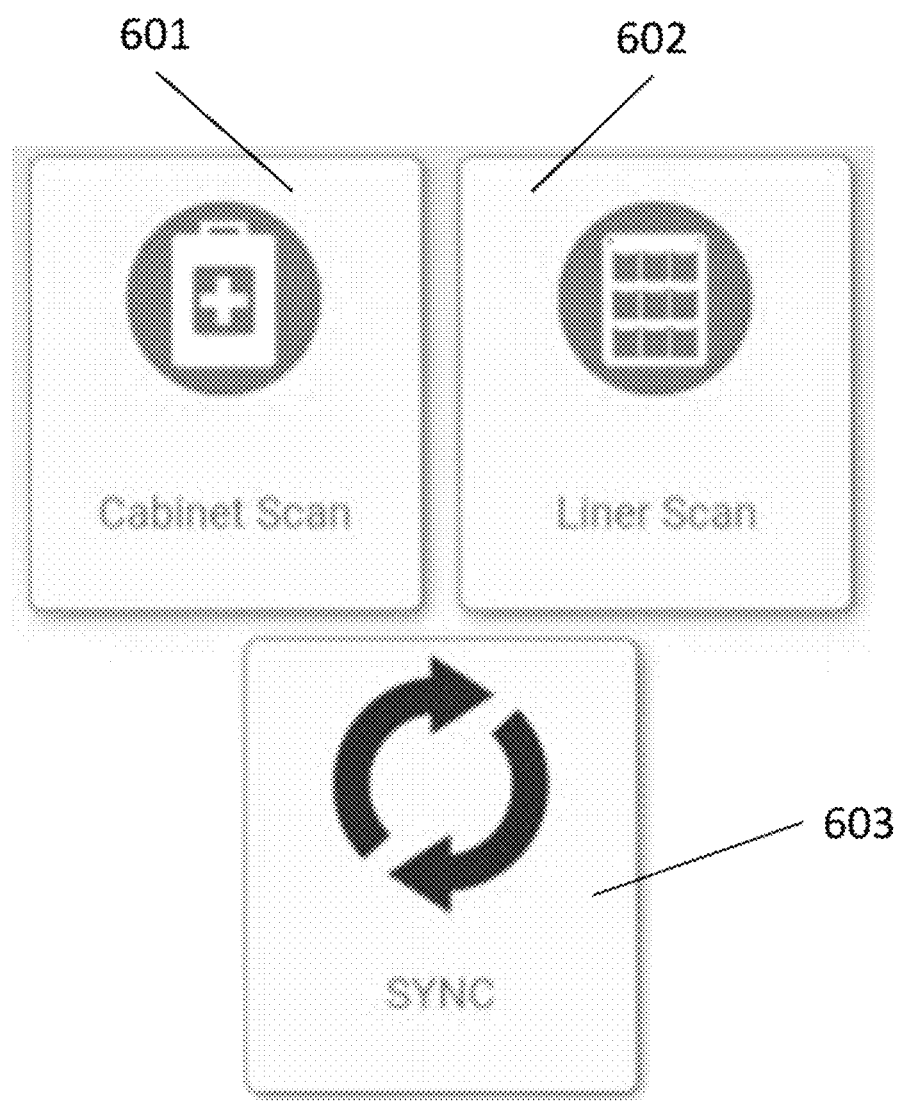
FIGS. 16-19 illustrate examples of an interface for the interface device of FIG. 15.

FIG. 16 illustrates touchscreen interfaces (activation areas) for the interface device 5000 of FIG. 15. As illustrated in FIG. 16, a touchscreen interface (activation area) 601 enables a user to initiate a full medical supply cabinet scan. Upon initiating such a scan, the radio frequency identification tag reader scans the medical supply cabinet for radio frequency identification tags and based upon the read radio frequency identification tags, the interface device can determine the identification of the medical supply cabinet as well as its contents and the status thereof.

As illustrated in FIG. 16, a touchscreen interface (activation area) 602 enables a user to initiate a medical supply liner scan. Upon initiating such a scan, the radio frequency identification tag reader scans the medical supply liner for radio frequency identification tags and based upon the read radio frequency identification tags, the interface device can determine the identification of the medical supply liner as well as its contents and the status thereof.

Lastly, as illustrated in FIG. 16, a touchscreen interface (activation area) 602 enables a user to initiate a syncing of the contents of a medical supply cabinet with a central database so as to update the database regarding the identification of the medical supply liner as well as its contents and the status thereof. Upon initiating the sync, the interface device uploads the scanned information to a central database to update the database.

Figure 17:
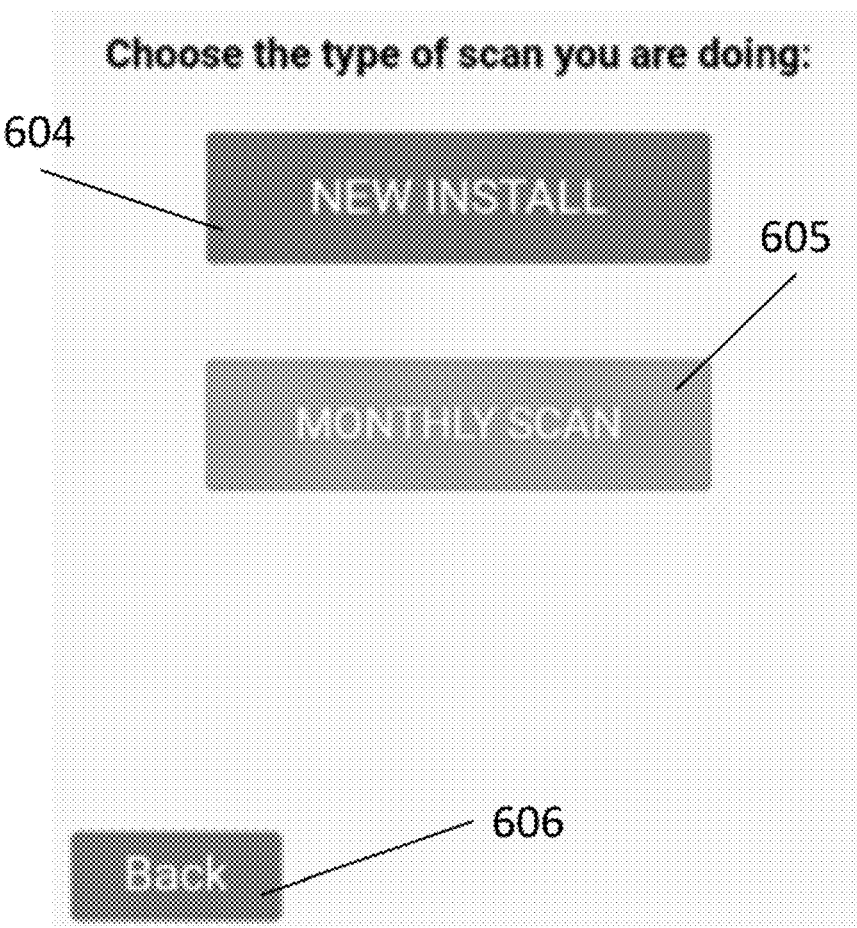

FIG. 17 illustrates touchscreen interfaces (activation areas) for the interface device 5000 of FIG. 15. As illustrated in FIG. 17, a touchscreen interface (activation area) 604 enables a user to initiate a full medical supply cabinet scan of a newly installed medical supply cabinet. Upon initiating such a scan, the radio frequency identification tag reader scans the medical supply cabinet for radio frequency identification tags and based upon the read radio frequency identification tags, the interface device can determine the identification of the medical supply cabinet as well as its contents and the status thereof. This new install function will create a new record in the central database when it is uploaded. The information may include the install date, the client (owner of the medical supply cabinet), the medical supply cabinet's identification, the location of the medical supply cabinet, the contents therein and the status thereof.

As illustrated in FIG. 17, a touchscreen interface (activation area) 605 enables a user to initiate a full medical supply cabinet monthly scan of a medical supply cabinet. Upon initiating such a scan, the radio frequency identification tag reader scans the medical supply cabinet for radio frequency identification tags and based upon the read radio frequency identification tags, the interface device can determine the identification of the medical supply cabinet as well as its contents and the status thereof. This new install function will create a new record in the central database when it is uploaded. The information can be utilized to determine the deficiencies of the medical supply cabinet; i.e., determine if the medical supply cabinet in compliance with regulations. Based upon the information, the deficient supplies in the medical supply cabinet can be replaced or replenished to bring the medical supply cabinet back in compliance with regulations.

Lastly, as illustrated in FIG. 17, a touchscreen interface (activation area) 605 enables a user to navigate to a previous touchscreen interface screen.

Figure 18:
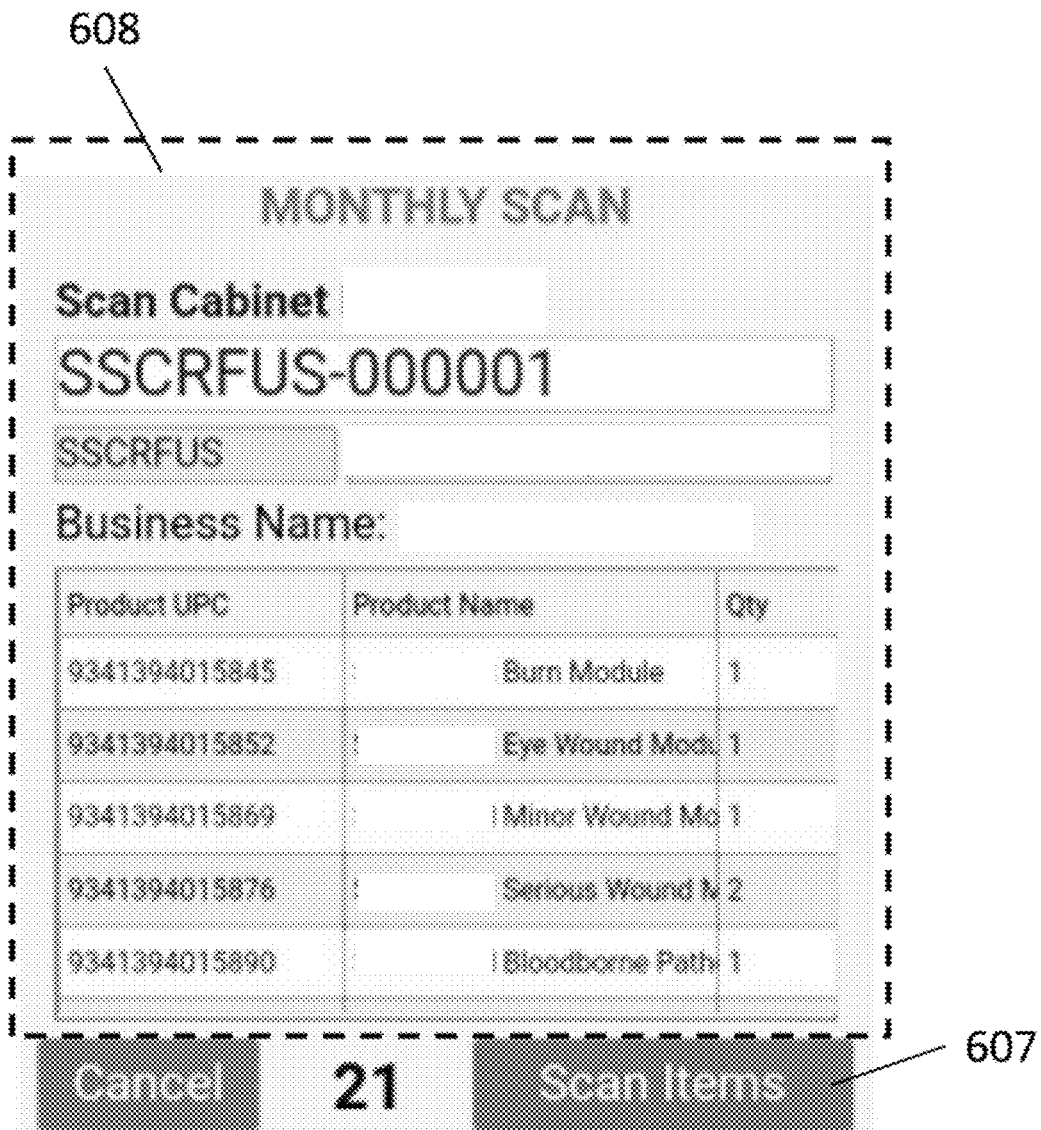

FIG. 18 illustrates a touchscreen interface that displays, in a display area 608, the identification of a medical supply cabinet (SSCRFUS-000001), a list of the requisite medical supplies for the identified medical supply cabinet, and a total number of requisite medical supplies for the identified medical supply cabinet (21). The touchscreen interface also includes a touchscreen interface (activation area) 607 to enable the user to initiate a full medical supply cabinet scan of a medical supply cabinet. Upon initiating such a scan, the radio frequency identification tag reader scans the medical supply cabinet for radio frequency identification tags and based upon the read radio frequency identification tags, the interface device can determine the contents of the medical supply cabinet as well as the status thereof.

Figure 19:
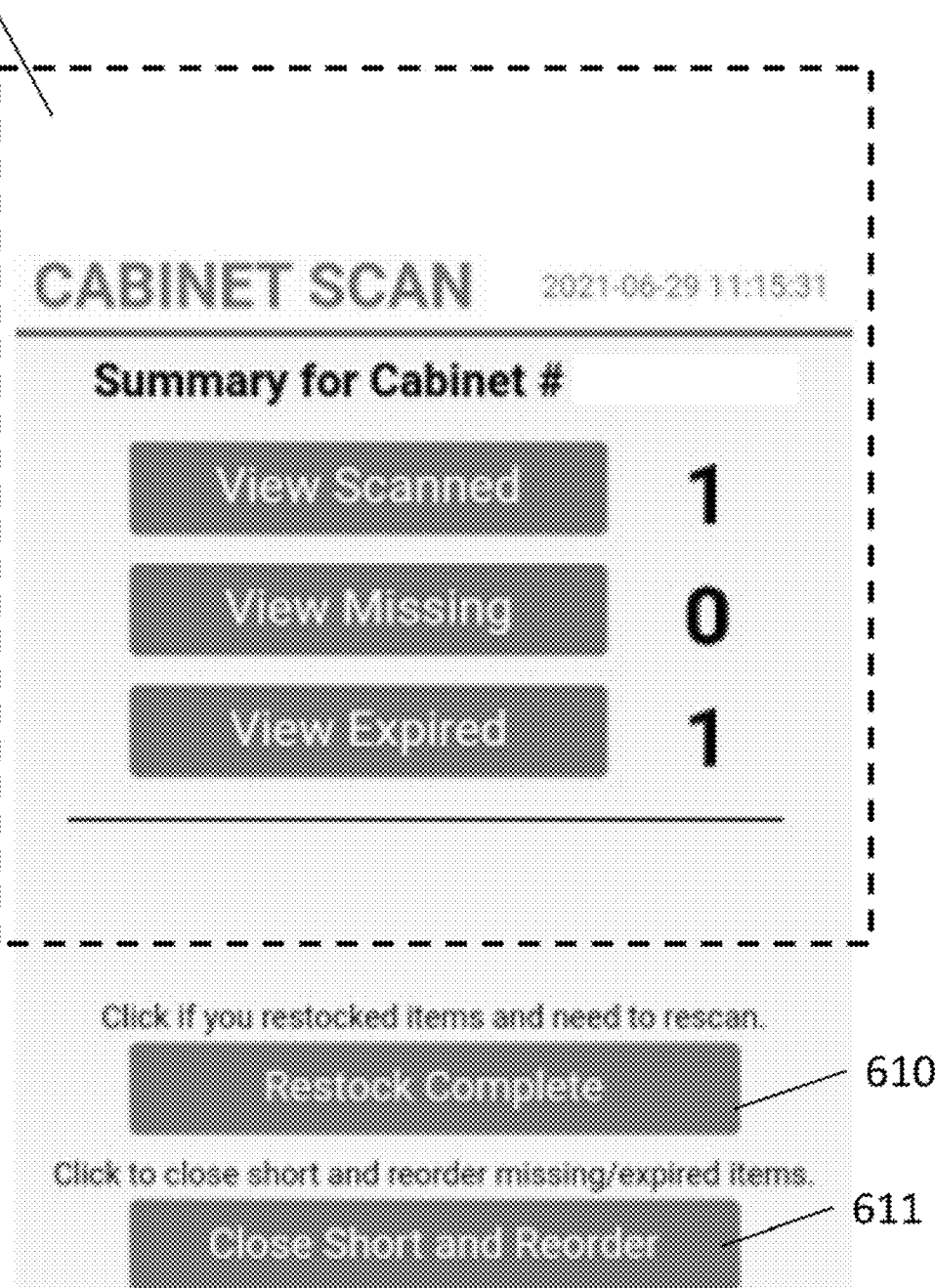

FIG. 19 illustrates a touchscreen interface that displays, in a display area 609, a summary of a scan of medical supply cabinet. As illustrated, the scan found one medical supply item, found that no medical supply items are missing, and found that the medical supply item has expired. Since the medical supply item has expired, the expired medical supply has to be replaced to bring the medical supply cabinet back in compliance with regulations.

If the expired medical supply is replaced, the user can activate touchscreen interface (activation area) 610 to initiate a full medical supply cabinet scan of the medical supply cabinet. The scan can then verify that the medical supply cabinet is in compliance with regulations and this information can be uploaded to the central database.

If the expired medical supply is not replaced, the user can activate touchscreen interface (activation area) 611 to initiate a closing of the audit and initiate a re-ordering of the expired medical supply item. This action keeps the state of the medical supply cabinet in non-compliance and initiates a re-ordering/servicing procedure to bring the medical supply cabinet back in compliance with regulations.

Figure 20:
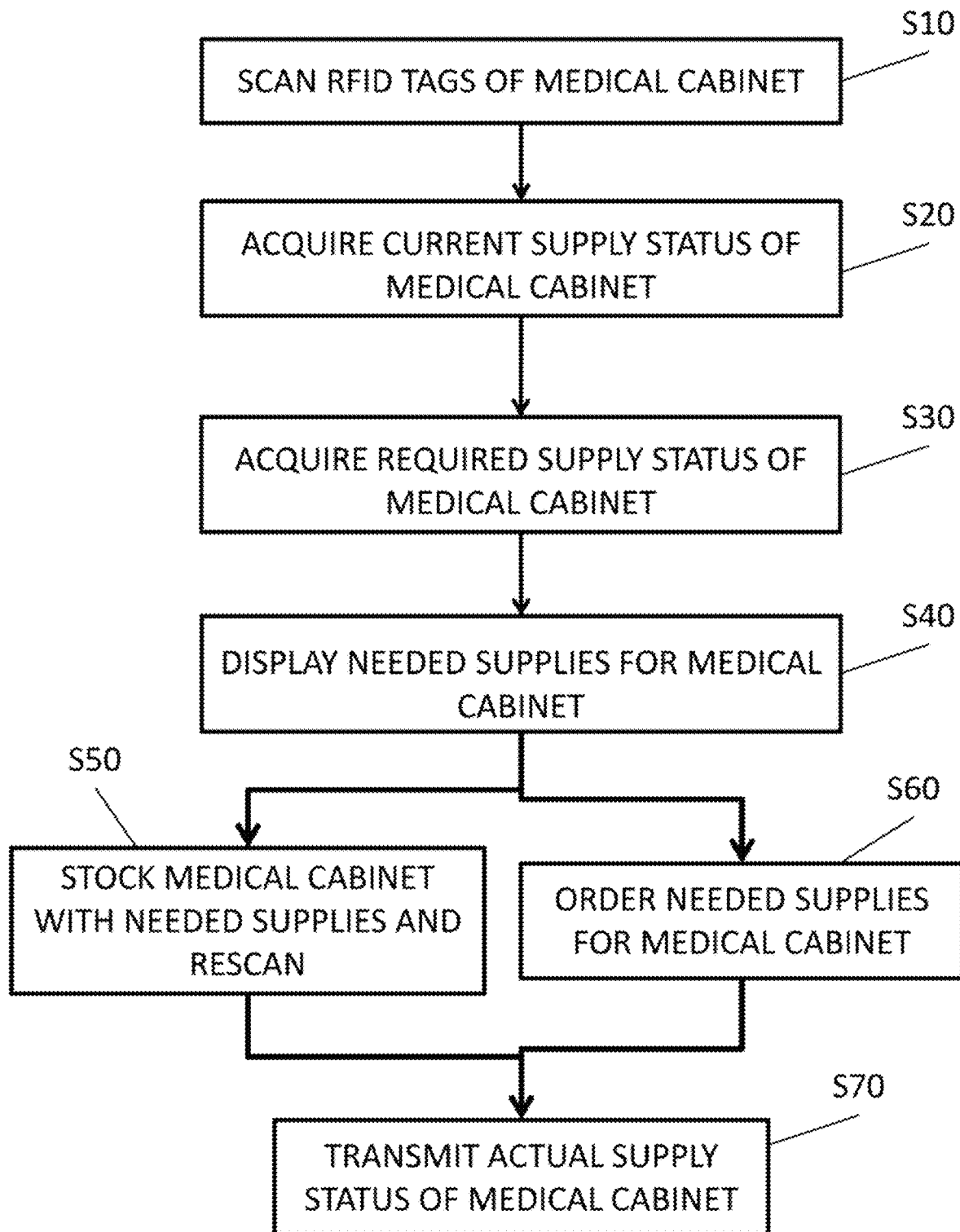
FIG. 20 illustrates a flowchart showing the inventory process for the medical supply cabinet.

FIG. 20 illustrates a flowchart showing the process for auditing the contents of a medical supply cabinet. As illustrated in FIG. 20, at step S10, the radio frequency identification tags of a medical supply cabinet are scanned (read). Based upon the scan, at step S20, the current supply status (present, missing, and/or expired) of the contents of medical supply cabinet are acquired. At step S30, the required supply status of the contents of medical supply cabinet is acquired, through the reading of a radio frequency identification tag that identifies the specific medical supply cabinet or by a user manually inputting the identification of the specific medical supply cabinet. The required supply status of the contents of medical supply cabinet can be retrieved, by the interface device, from a central database or can be pre-loaded onto the interface device.

At step S40, based upon a comparison of the current supply status of the contents of medical supply cabinet, acquired at step S20, and the required supply status of the contents of medical supply cabinet, acquired at step S30, the needed supplies to bring the medical supply cabinet back in compliance with regulations is displayed. This information can be used by the user to replace or replenish the necessary medical supplies.

If needed the missing and/or expired medical supplies are replaced, at step S50, the medical supply cabinet is rescanned to verify that the medical supply cabinet is in compliance with regulations and this information can be uploaded to the central database, at step S70.

If needed the missing and/or expired medical supplies are not replaced, at step S60, the needed medical supplies are ordered and this information can be uploaded to the central database, at step S70.

The used of radio frequency identification tags and the radio frequency identification tag reader allows a verifiable audit of the contents of a medical supply cabinet and the status of each supply item.

If the supply item is missing or some portion of the supply item has been used because the corresponding radio frequency identification tag has been discarded, the radio frequency identification tag audit can identify the deficient supply item so that it can be readily replaced and the medical supply cabinet brought back in compliance with regulations.

If the supply item is expired based on the information associated with the corresponding radio frequency identification tag, the radio frequency identification tag audit can identify the expired supply item so that it can be readily replaced and the medical supply cabinet brought back in compliance with regulations.

The used of radio frequency identification tags and the radio frequency identification tag reader allows the maintenance of a database that enables efficient servicing of the medical supply cabinets.

It is noted that although the various embodiments described above use visually machine readable codes or graphics, the machine readable code or graphic may be a RFID tag to identify the medical module, medical supply, and/or container of medicine.

It is further noted that although the various embodiments described above use transparent pouches on the removable liner, the pouches may be non-transparent so long as the pouches do not visually impede the visually machine readable codes or graphics.

In summary, a medical supply cabinet includes a removable liner that attaches to the door. The removable liner, on a first side, has a plurality of pouches and associated machine readable codes or graphics to identify the particular medical supply for the particular pouch. The machine readable codes or graphics on the first side of the removable liner are located on the removable liner so as to be only visible when the associated medical supply needs replenishing.

The inclusion of the associated visually machine readable codes or graphics on the first side of the removable liner provides a redundant (fail-safe) mechanism to enable an accurate identification of which medical supplies have been depleted and need replenishing.

The removable liner, on a second side, has a plurality of machine readable codes or graphics associated with medical modules and/or containers of medicine located in the cabinet storage volume. The machine readable codes or graphics on the second side of the removable liner are located on the removable liner so as to be associated with the locations of medical modules and/or containers of medicine in the cabinet storage volume.

The inclusion of the associated visually machine readable codes or graphics on the second side of the removable liner provides a redundant (fail-safe) mechanism to enable an accurate identification of which medical modules have been depleted and need replenishing.

A medical supply cabinet, comprises a housing; a medical supply cabinet identifying radio frequency identification tag located on the housing; and a plurality of medical supply packages, each medical supply package containing a specific medical supply; each medical supply package including a discarded portion created when the medical supply package is opened; the discarded portion of the medical supply package including a medical supply package radio frequency identification tag identifying the specific medical supply associated with the medical supply package.

The medical supply package radio frequency identification tag may identify an expiration date of the specific medical supply associated with the medical supply package.

The discarded portion of the medical supply package may be a tear-away portion of the medical supply package.

The discarded portion of the medical supply package may be a shrink-wrap around the medical supply package.

A system for auditing contents of a medical supply cabinet, comprises a housing; a medical supply cabinet identifying radio frequency identification tag located on the housing; a plurality of medical supply packages, each medical supply package containing a specific medical supply; and a radio frequency identification tag reader; each medical supply package including a discarded portion created when the medical supply package is opened; the discarded portion of the medical supply package including a medical supply package radio frequency identification tag identifying the specific medical supply associated with the medical supply package; the radio frequency identification tag reader reading the medical supply cabinet identifying radio frequency identification tag and the medical supply package radio frequency identification tags; the radio frequency identification tag reader determining, based upon the read medical supply cabinet identifying radio frequency identification tag and medical supply package radio frequency identification tags, which specific medical supplies are in the medical supply cabinet, which specific medical supplies in the medical supply cabinet are expired, and which specific medical supplies in the medical supply cabinet are missing.

The medical supply package radio frequency identification tag may identify an expiration date of the specific medical supply associated with the medical supply package.

The discarded portion of the medical supply package may be a tear-away portion of the medical supply package.

The discarded portion of the medical supply package may be a shrink-wrap around the medical supply package.

A method for auditing contents of a medical supply cabinet having a medical supply cabinet identifying radio frequency identification tag located thereon and a plurality of medical supply packages, each medical supply package containing a specific medical supply and a medical supply package radio frequency identification tag identifying the specific medical supply associated with the medical supply package, comprises (a) reading the a medical supply cabinet identifying radio frequency identification tag and the medical supply package radio frequency identification tags; (b) determining, based upon the read medical supply package radio frequency identification tags, the current supply status of the medical supplies in the medical supply cabinet; (c) determining, based upon the read medical supply cabinet identifying radio frequency identification tag, the required supply status of the medical supplies in the medical supply cabinet; (d) comparing the current supply status of the medical supplies in the medical supply cabinet and the required supply status of the medical supplies in the medical supply cabinet; (e) determining, based upon the comparison of the current supply status of the medical supplies in the medical supply cabinet and the required supply status of the medical supplies in the medical supply cabinet, the needed supplies for the medical supply cabinet; (f) reading the medical supply cabinet identifying radio frequency identification tag and the medical supply package radio frequency identification tags, if the needed supplies for the medical supply cabinet are replaced, to verify that the medical supply cabinet is in compliance with regulations and to determine a revised current supply status of the medical supplies in the medical supply cabinet; and (g) uploading the revised current supply status of the medical supplies in the medical supply cabinet to a database.

Each medical supply package may include a discarded portion created when the medical supply package is opened.

The medical supply package radio frequency identification tag may identify an expiration date of the specific medical supply associated with the medical supply package.

The discarded portion of the medical supply package may be a tear-away portion of the medical supply package.

The discarded portion of the medical supply package may be a shrink-wrap around the medical supply package.

It will be appreciated that variations of the above-disclosed embodiments and other features and functions, or alternatives thereof, may be desirably combined into many other different systems or applications. Also, various presently unforeseen or unanticipated alternatives, modifications, variations, or improvements therein may be subsequently made by those skilled in the art which are also intended to be encompassed by the description above.

What is claimed is:

1. A system for auditing contents of a medical supply cabinet, comprising:
a housing comprising a cabinet storage volume and a door;
a medical supply cabinet identifying radio frequency identification (RFID) tag located on the housing;
a first plurality of medical supply packages configured to be stored in the cabinet storage volume, each of the first plurality of medical supply packages containing a specific medical supply; and
a removable liner on the door, comprising:
a second plurality of medical supply packages;
a first side comprising a plurality of pouches and a plurality of pouch machine-readable codes, each pouch configured to store one of the second plurality of medical supply packages,
wherein each of the plurality of pouch machine-readable codes is located on the removable liner such that a medical supply package in a pouch of the plurality of pouches obscures a corresponding pouch machine-readable code and exposes the corresponding pouch machine-readable code when the medical supply package is removed from the pouch; and
a second side comprising a plurality of cabinet machine-readable codes corresponding to the first plurality of medical supply packages; and
a reader,
wherein each medical supply package includes a discarded portion created when the medical supply package is opened;
wherein the discarded portion of the medical supply package includes a medical supply package RFID tag identifying the specific medical supply associated with the medical supply package;
wherein the reader is configured to read the medical supply cabinet identifying RFID tag, the medical supply package RFID tags, the plurality of pouch machine-readable codes, and the plurality of cabinet machine-readable codes;
wherein the reader is configured to determine, based upon the read medical supply cabinet identifying RFID tags, the read medical supply package RFID tags, one or more exposed pouch machine-readable codes, and one or more read cabinet machine-readable codes, which specific medical supplies are in the medical supply cabinet, which specific medical supplies in the medical supply cabinet are expired, and which specific medical supplies in the medical supply cabinet are missing.

2. The system of claim 1, wherein the medical supply package RFID tag identifies an expiration date of the specific medical supply associated with the medical supply package.

3. The system of claim 1, wherein the discarded portion of the medical supply package is a tear-away portion of the medical supply package.

4. The system of claim 1, wherein the discarded portion of the medical supply package is a shrink-wrap around the medical supply package.

5. The system of claim 1, wherein each of the plurality of cabinet machine-readable codes on the second side of the removable liner is in a location corresponding to a location of a corresponding medical supply package of the first plurality of medical supply packages.

6. The system of claim 1, further comprising:
an interface device communicatively coupled to the reader and configured to display the specific medical supplies in the cabinet that are missing.

7. The system of claim 6, wherein the interface device is configured to display an activation area that, when actuated, initiates a re-ordering of the specific medical supplies in the medical supply cabinet that are expired.

8. A method for auditing contents of a medical supply cabinet having a medical supply cabinet identifying radio frequency identification (RFID) tag located thereon and a plurality of medical supply packages, each medical supply package containing a specific medical supply and a medical supply package (RFID) tag identifying the specific medical supply associated with the medical supply package, the method comprising:
reading, with an RFID reader, the medical supply cabinet identifying RFID tag and the medical supply package RFID tags,
wherein each medical supply package comprises a discarded portion having the medical supply package RFID tag thereon,
wherein at least one medical supply package is located in a removable liner of the medical supply cabinet,
wherein the removable liner comprises:
a first side having a plurality of pouches, each pouch configured to store a pouch medical supply of the plurality of medical supplies therein;
a plurality of pouch machine-readable codes, each pouch machine-readable code corresponding to a pouch such that the pouch machine-readable code is obscured when the pouch medical supply is in the pouch and the pouch machine-readable code is machine-readable when the pouch medical supply is removed from the pouch; and
wherein the medical supply cabinet identifying RFID tag is associated with a list of the plurality of medical supply packages configured to be stored in the medical supply cabinet;
reading, with a machine-readable code reader, one or more exposed pouch machine-readable codes;
determining, based upon the read medical supply package RFID tags and the one or more exposed pouch machine-readable codes, a current supply status of the medical supplies in the medical supply cabinet;
determining, based upon the read medical supply cabinet identifying RFID tag, a required supply status of the medical supplies in the medical supply cabinet,
wherein determining the required supply status is further based on comparing one or more medical supply package RFID tags that were not scanned to the list of the plurality of medical supply packages configured to be stored in the medical supply cabinet;
comparing the current supply status of the medical supplies in the medical supply cabinet and the required supply status of the medical supplies in the medical supply cabinet;
determining, based upon the comparing of the current supply status of the medical supplies in the medical supply cabinet and the required supply status of the medical supplies in the medical supply cabinet, one or more needed supplies for the medical supply cabinet;
after replacing the one or more needed supplies in the medical supply cabinet, reading the medical supply cabinet identifying RFID tag and the medical supply package RFID tags to verify that the medical supply cabinet is in compliance with regulations and to determine a revised current supply status of the medical supplies in the medical supply cabinet; and uploading the revised current supply status of the medical supplies in the medical supply cabinet to a database.

9. The method of claim 8, wherein each medical supply package includes a discarded portion created when the medical supply package is opened.

10. The method of claim 8, wherein the medical supply package radio frequency identification tag identifies an expiration date of the specific medical supply associated with the medical supply package.

11. The method of claim 9, wherein the discarded portion of the medical supply package is a tear-away portion of the medical supply package.

12. The method of claim 9, wherein the discarded portion of the medical supply package is a shrink-wrap around the medical supply package.

13. The method of claim 8, further comprising:
causing display of one or more expired medical supplies and an activation area on an interface device associated with the RFID reader; and
responsive to detecting an actuation of the activation area, initiating a re-ordering of the one or more expired medical supplies.

14. The method of claim 8, wherein the removable liner is removably attachable to a door of the medical supply cabinet.

15. The method of claim 8, wherein the removable liner further comprises a second side comprising a plurality of cabinet machine-readable codes, each of the plurality of cabinet machine-readable codes located on the second side of the removable liner at a position corresponding to a position of a corresponding medical supply in a cabinet storage volume of the medical supply cabinet.

16. A medical supply cabinet, comprising:
a housing comprising:
a medical supply cabinet identifying RFID tag associated with a list of a plurality of medical supplies configured to be stored in the medical supply cabinet;
a door;
a removable liner on the door, comprising:
a first side having a plurality of pouches, each pouch configured to store a pouch medical supply of the plurality of medical supplies therein;
a plurality of pouch machine-readable codes, each pouch machine-readable code corresponding to a pouch such that the pouch machine-readable code is obscured when the pouch medical supply is in the pouch and the pouch machine-readable code is machine-readable when the pouch medical supply is removed from the pouch; and
a cabinet storage volume configured to store at least one cabinet medical supply of the plurality of medical supplies,
wherein the at least one cabinet medical supply comprises a discardable portion having a cabinet package RFID tag thereon,
wherein the medical supply cabinet identifying RFID tag, one or more exposed pouch machine-readable codes, and one or more cabinet medical supplies are configured to be scanned by a reader to determine one or more needed supplies, and
wherein determining the one or more needed supplies is based on a comparison of the list of the plurality of medical supplies configured to be stored in the medical supply cabinet, the one or more exposed machine-readable codes, and one or more unscanned cabinet package RFID tags.

17. The medical supply cabinet of claim 16, wherein the cabinet package RFID tag identifies an expiration date of the at least one cabinet medical supply, and wherein the pouch machine-readable code identifies an expiration date of the pouch medical supply.

18. The medical supply cabinet of claim 16, wherein the discarded portion of the cabinet medical supply is a tear-away portion.

19. The medical supply cabinet of claim 16, wherein the discarded portion of the cabinet medical supply is a shrink-wrap around the cabinet medical supply.

20. The medical supply cabinet of claim 16, wherein the removable liner further comprises a second side comprising a plurality of cabinet machine-readable codes, each of the second plurality of cabinet machine-readable codes located on the second side of the removable liner at a position corresponding to a position of a corresponding cabinet medical supply in the cabinet storage volume.

* * * * *